(12) United States Patent
Altounian et al.

(10) Patent No.: US 11,744,933 B2
(45) Date of Patent: Sep. 5, 2023

(54) SALIVA MANAGEMENT SYSTEM

(71) Applicant: Neavso Solutions LLC, Keego Harbor, MI (US)

(72) Inventors: Jennifer Rebecca Altounian, White Lake, MI (US); Cheryl Sawicki, Royal Oak, MI (US); Laura Foos, Plymouth, MI (US)

(73) Assignee: Saliva Management Systems, Inc., Keego Harbor, MI (US)

( * ) Notice: Subject to any disclaimer, the term of this patent is extended or adjusted under 35 U.S.C. 154(b) by 588 days.

(21) Appl. No.: 16/722,854

(22) Filed: Dec. 20, 2019

(65) Prior Publication Data

US 2020/0214815 A1 Jul. 9, 2020

Related U.S. Application Data

(63) Continuation-in-part of application No. 16/052,860, filed on Aug. 2, 2018, now abandoned, which is a continuation-in-part of application No. 15/373,555, filed on Dec. 9, 2016, now abandoned.

(60) Provisional application No. 62/913,444, filed on Oct. 10, 2019, provisional application No. 62/783,562, filed on Dec. 21, 2018, provisional application No. 62/265,172, filed on Dec. 9, 2015.

(51) Int. Cl.
*A61C 17/06* (2006.01)
*A61M 1/00* (2006.01)

(52) U.S. Cl.
CPC .............. *A61M 1/85* (2021.05); *A61C 17/06* (2019.05); *A61M 1/77* (2021.05); *A61M 2202/0466* (2013.01); *A61M 2205/3331* (2013.01); *A61M 2210/0631* (2013.01)

(58) Field of Classification Search
CPC ....... A61C 17/06; A61C 17/08; A61C 19/063; A61C 19/001; A61C 17/092; A61C 17/096; A61C 17/10; A61M 1/85; A61M 1/0058
See application file for complete search history.

(56) References Cited

U.S. PATENT DOCUMENTS

| | | |
|---|---|---|
| 522,842 A | 7/1894 | Lawshe |
| 1,986,751 A | 1/1935 | Robinson |
| 2,161,151 A | 6/1939 | Freedman |

(Continued)

FOREIGN PATENT DOCUMENTS

EP 0468926 A1 1/1992

OTHER PUBLICATIONS

Xeros Dry Mouth Pump FAQ, http://drymouthpump.com/, 2008, 3 pages.

(Continued)

*Primary Examiner* — Courtney B Fredrickson
(74) *Attorney, Agent, or Firm* — Rocklaw PLLC; Michael T. Fluhler

(57) ABSTRACT

A saliva management system may be configured to manage fluid transfer with respect to first and second bodily regions. The system may include an anchoring member and a connector member. The anchoring member may be configured conformingly engage the first and second bodily regions. The connector member may include a capture portion and a fluid transfer portion. The capture portion may be configured to receive a central portion of the anchoring member. The fluid transfer portion may be being fluidically connected to a supply source.

20 Claims, 39 Drawing Sheets

(56) References Cited

U.S. PATENT DOCUMENTS

| | | | |
|---|---|---|---|
| 2,180,249 A | 11/1939 | Lempert | |
| 2,504,557 A | 4/1950 | Lumian | |
| 2,507,938 A | 5/1950 | Smith | |
| 2,701,916 A * | 2/1955 | Jarboejohnp | A61C 17/08 433/96 |
| 2,957,476 A | 10/1960 | Freeman | |
| 3,060,935 A | 10/1962 | Riddell | |
| 3,379,192 A | 4/1968 | Warren | |
| 3,504,666 A | 4/1970 | Vireno | |
| 3,516,402 A | 6/1970 | Toth | |
| 3,520,300 A | 7/1970 | Flowers, Jr. | |
| 3,731,675 A | 5/1973 | Kelly | |
| 3,758,950 A | 9/1973 | Krouzian | |
| 3,834,226 A | 9/1974 | Pecorella et al. | |
| 3,864,831 A | 2/1975 | Drake | |
| 3,991,471 A | 11/1976 | Hoops | |
| 4,164,940 A | 8/1979 | Quinby | |
| 4,173,505 A | 11/1979 | Jacobs | |
| 4,233,025 A | 11/1980 | Larson et al. | |
| 4,299,568 A | 11/1981 | Crowley | |
| 4,560,351 A | 12/1985 | Osborne | |
| 4,764,115 A | 8/1988 | Willits et al. | |
| 4,838,882 A | 6/1989 | Molinoff | |
| 4,917,674 A | 4/1990 | Molinoff | |
| 5,018,967 A | 5/1991 | Schwalbach | |
| 5,055,108 A | 10/1991 | Jenkins | |
| 5,057,077 A | 10/1991 | Turner et al. | |
| 5,071,347 A | 12/1991 | McGuire | |
| 5,078,129 A | 1/1992 | Kleinberg et al. | |
| 5,083,919 A | 1/1992 | Quach | |
| 5,094,616 A | 3/1992 | Levenson | |
| 5,104,315 A | 4/1992 | McKinley | |
| 5,364,269 A | 11/1994 | Willits et al. | |
| 5,484,405 A | 1/1996 | Edstrom, Sr. | |
| 5,509,801 A | 4/1996 | Nicholson | |
| 5,512,045 A | 4/1996 | Gurchumelidze | |
| 5,512,293 A | 4/1996 | Landrau et al. | |
| 5,529,214 A | 6/1996 | Lasonde et al. | |
| 5,731,338 A | 3/1998 | Acharya | |
| 5,741,805 A | 4/1998 | Acharya | |
| 5,749,898 A | 5/1998 | Schulze et al. | |
| 5,980,498 A | 11/1999 | Brown et al. | |
| 5,984,145 A | 11/1999 | McAllister | |
| 6,000,395 A | 12/1999 | Brown | |
| 6,068,477 A * | 5/2000 | Mahlmann | A61C 17/08 433/136 |
| 6,267,596 B1 | 7/2001 | Kalfas | |
| 6,283,344 B1 | 9/2001 | Bradley | |
| 6,652,481 B1 | 11/2003 | Brown et al. | |
| 6,893,259 B1 | 5/2005 | Reizenson | |
| 6,896,516 B2 | 5/2005 | Lin et al. | |
| 7,118,377 B2 | 10/2006 | Inoue et al. | |
| 7,347,691 B1 | 3/2008 | Kelly, Sr. | |
| 8,122,889 B2 | 2/2012 | Vaska et al. | |
| 8,371,853 B2 | 2/2013 | Levine | |
| 8,464,709 B2 | 6/2013 | Wedemeyer | |
| 8,684,956 B2 | 4/2014 | McDonough et al. | |
| 8,979,823 B2 | 3/2015 | Podmore et al. | |
| 9,044,293 B2 | 6/2015 | Reyes | |
| 9,414,899 B2 | 8/2016 | Altounian | |
| 9,597,278 B2 | 3/2017 | Hamlin | |
| 9,884,082 B2 | 2/2018 | Hamlin | |
| 2003/0091210 A1 | 5/2003 | Baskerville | |
| 2005/0064370 A1 | 3/2005 | Duret | |
| 2007/0204867 A1 | 9/2007 | Kennedy et al. | |
| 2008/0171303 A1 | 7/2008 | Roberts et al. | |
| 2008/0272153 A1 | 11/2008 | Hochstadter et al. | |
| 2009/0092643 A1 | 4/2009 | De Vreese et al. | |
| 2009/0123886 A1 * | 5/2009 | Vaska | A61F 5/566 433/91 |
| 2009/0208898 A1 | 8/2009 | Kaplan | |
| 2010/0084432 A1 | 4/2010 | Pelfrey | |
| 2012/0082955 A1 | 4/2012 | Yang | |
| 2012/0199135 A1 | 8/2012 | Podmore et al. | |
| 2013/0025607 A1 | 1/2013 | Altounian | |
| 2014/0014112 A1 | 1/2014 | Vitale et al. | |
| 2017/0151399 A1 | 6/2017 | Vaska et al. | |
| 2017/0216085 A1 | 8/2017 | Vaska et al. | |
| 2017/0216148 A1 | 8/2017 | Altounian | |
| 2020/0171221 A1 * | 6/2020 | Zhu | A61M 1/84 |

OTHER PUBLICATIONS

Xeros Dry Mouth Pump, http://www.craniorehab.com/xeros-system.html, 2018, 4 pages.

History, Theory and Development of the Xeros Dry Mouth Pump, Mar. 8, 2013, 1 page.

Devilbiss Homecare Suction Unit with Battery, http://healthproductsforyou.com/p-3773-devilbiss-homecare-suction-unit-wi-th-battery.ht . . . ,2 pages, 2013.

Invacare Aspirator, http://www.invacare.com/cgi-bin/imhqprd/inv.sub-catalog/prod.sub.-cat.-detail.jsp?prodID=IRC1135, 2 pages, 2013.

IsoliteSystems, http://www.isolitesystems.com/explore-dental-isolation-systems/select-the-right-system-for-you-/isolite, 2 pages, 2013.

Allied Healthcare Products Inc., DC Portable Aspirator Operation/Service Manual, Gomco G180 Portable Suction Device, Https://ww.alliedhpi.com/images/zs168-507-001.sub.-h.pdf, 13 pages, 2013.

Non-Final Office Action for corresponding Action No. 15373555 dated Dec. 20, 2018.

* cited by examiner

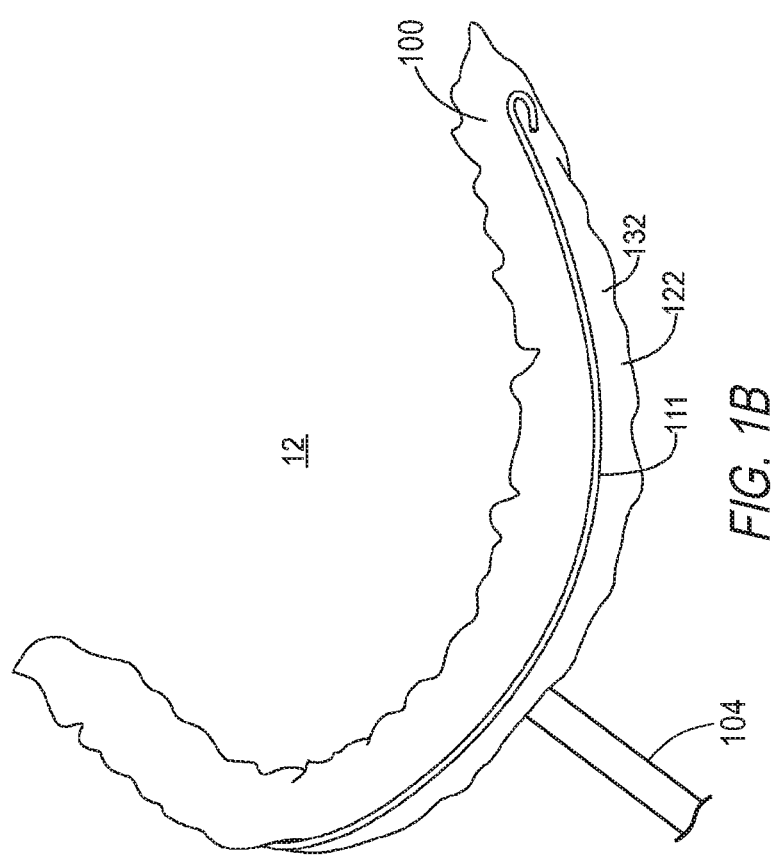

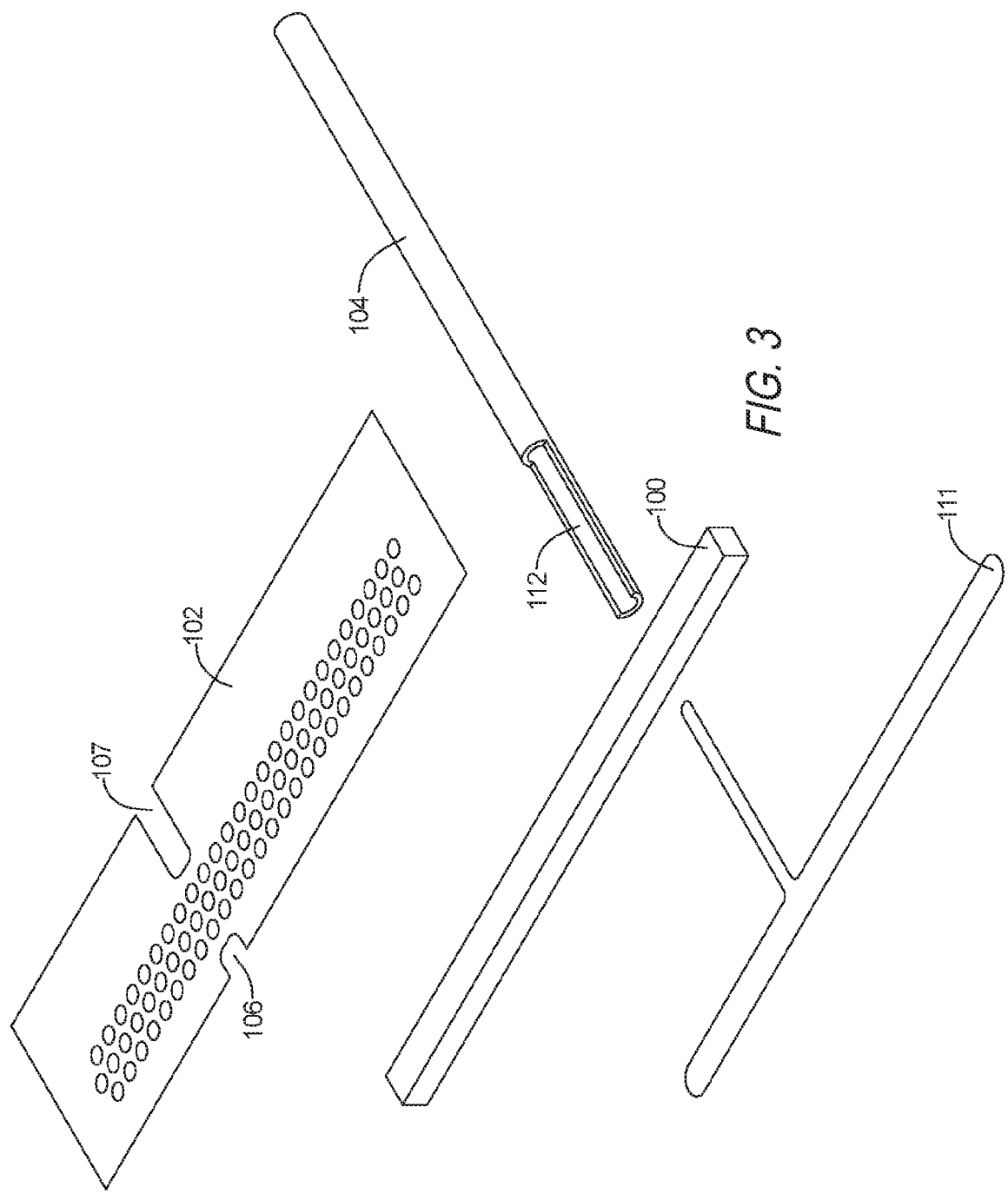

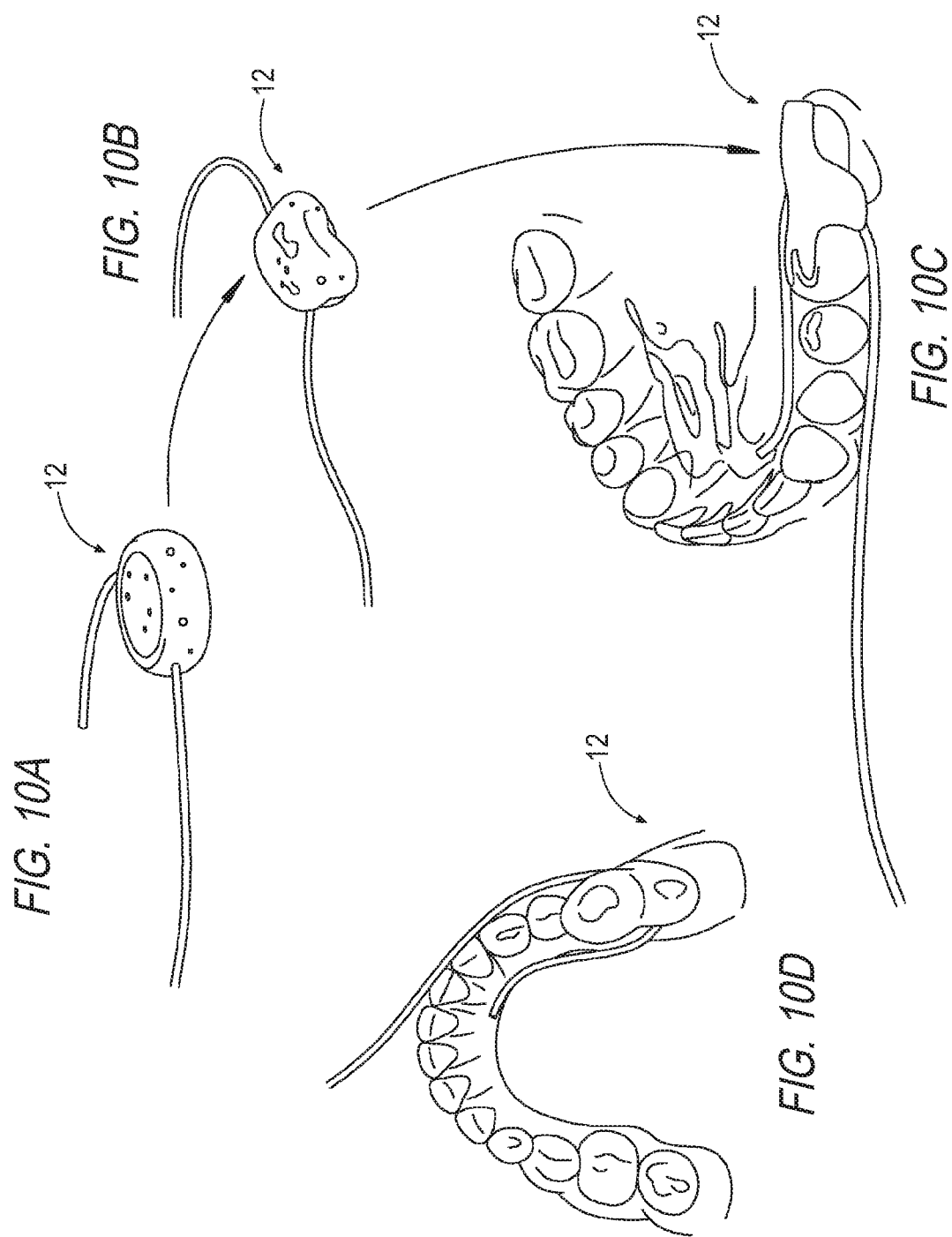

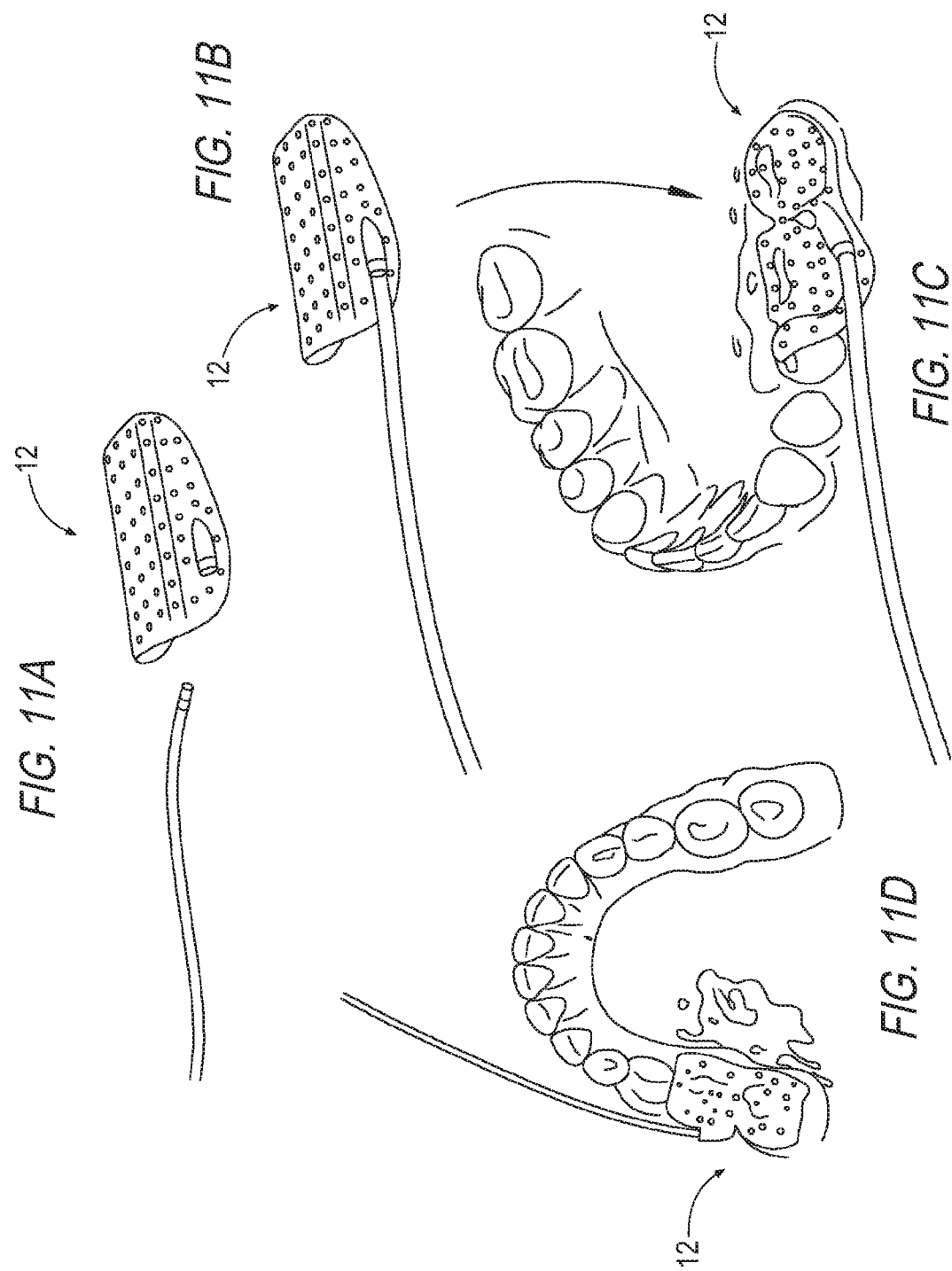

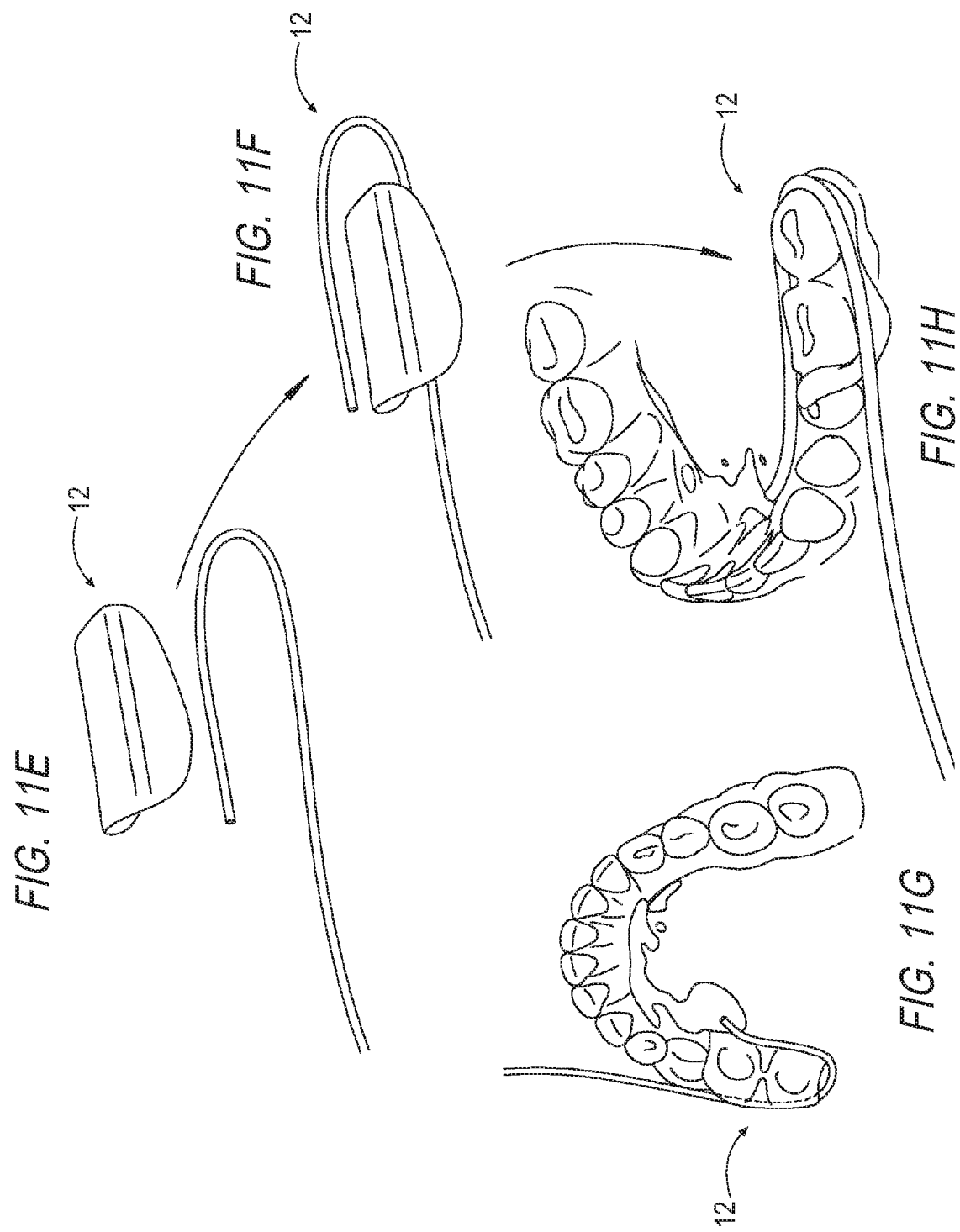

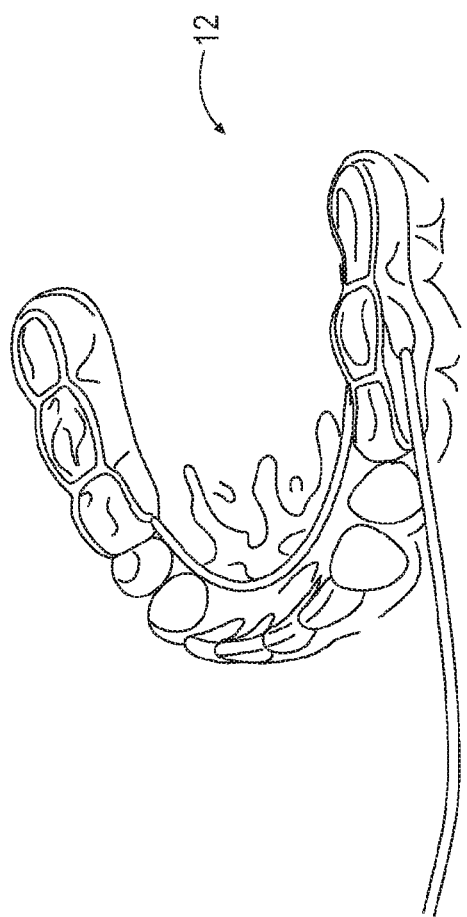
FIG.12D
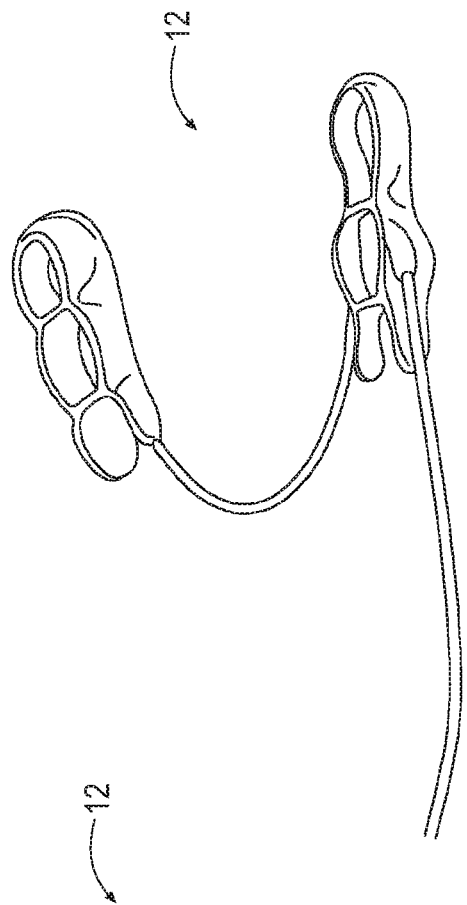
FIG.12E
FIG.12F

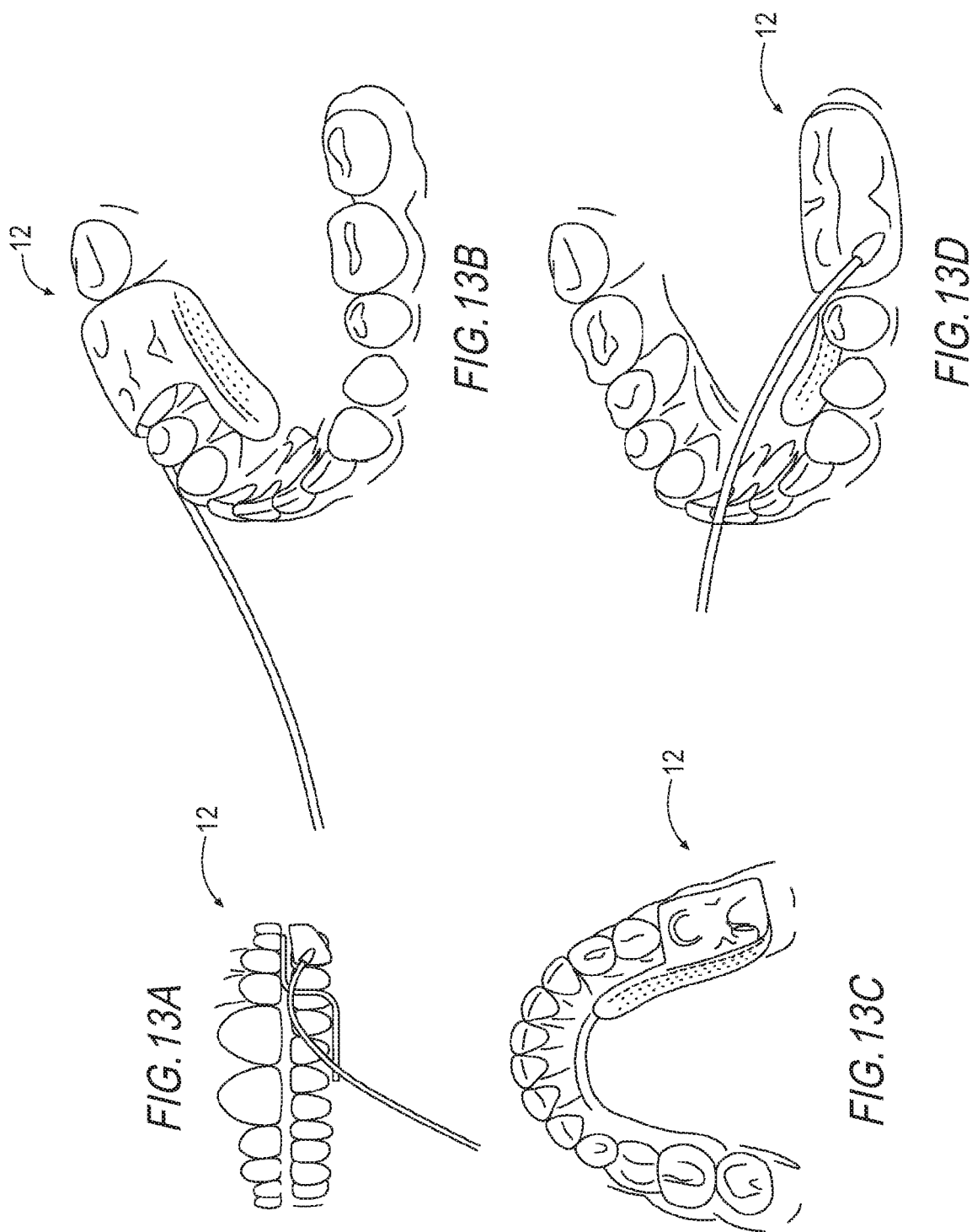

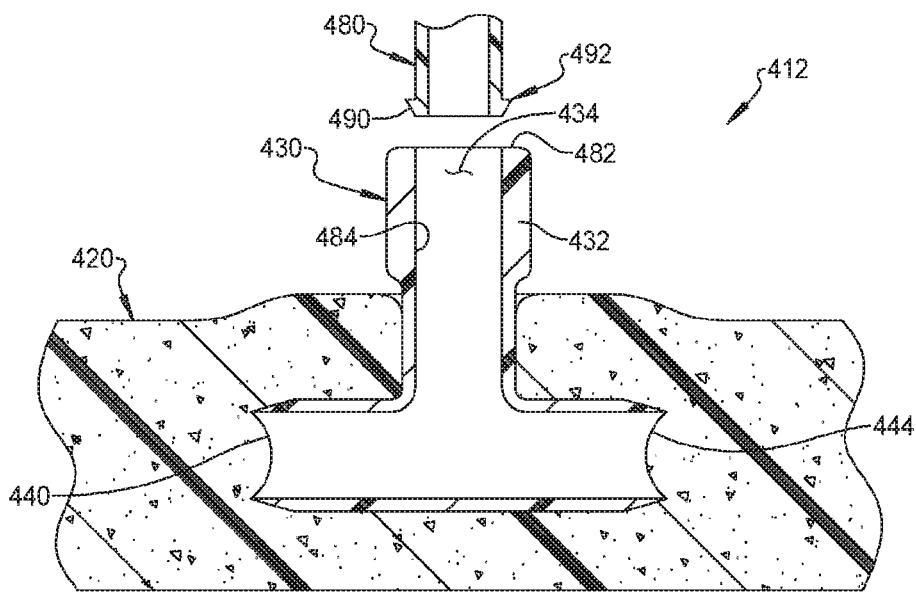
FIG.18
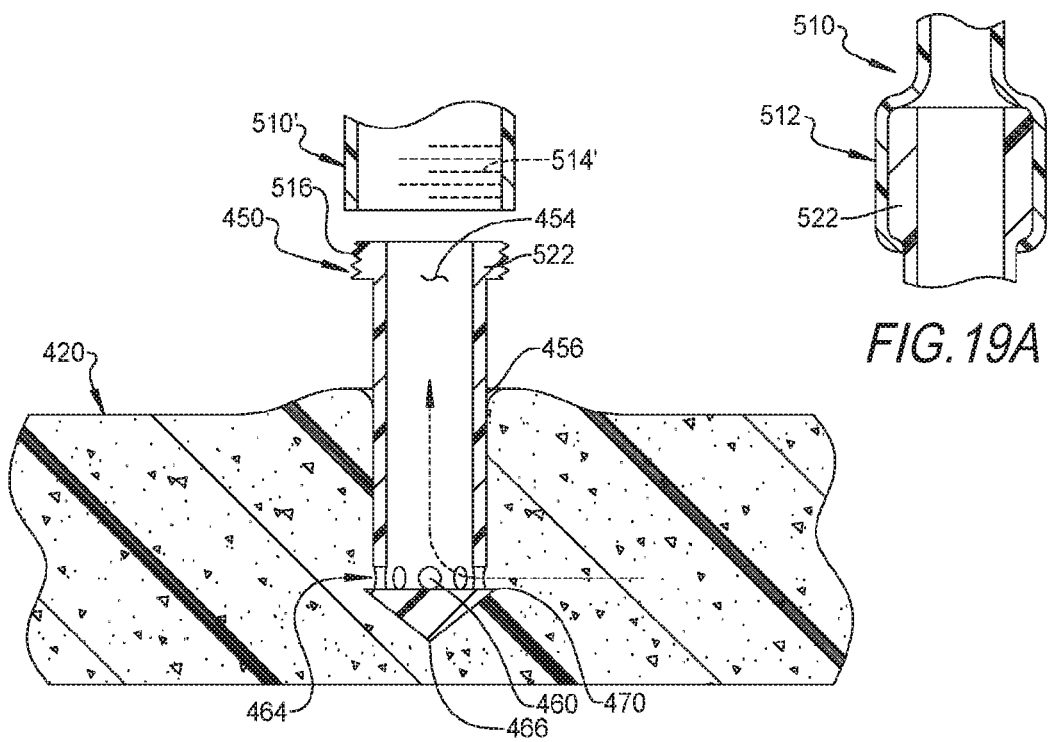
FIG.19
FIG.19A

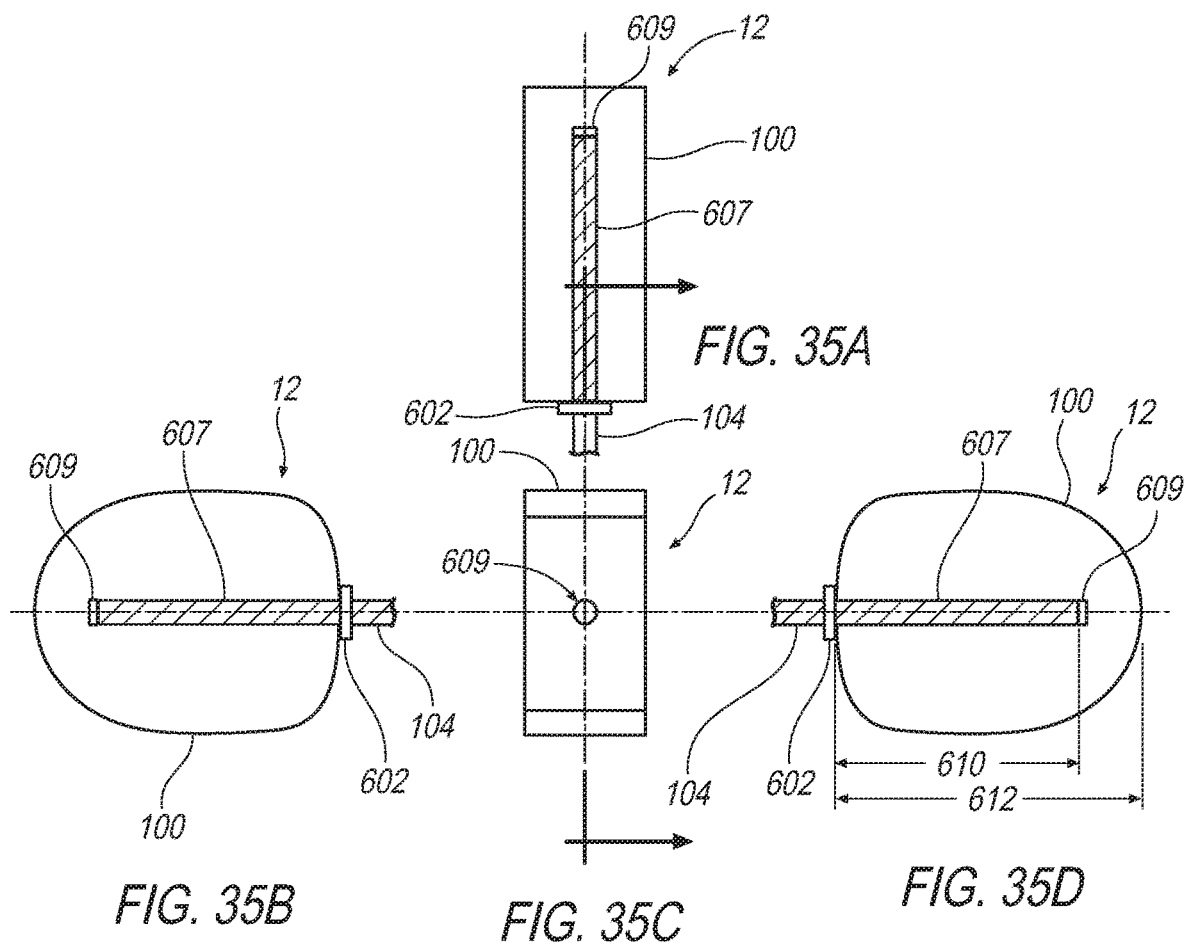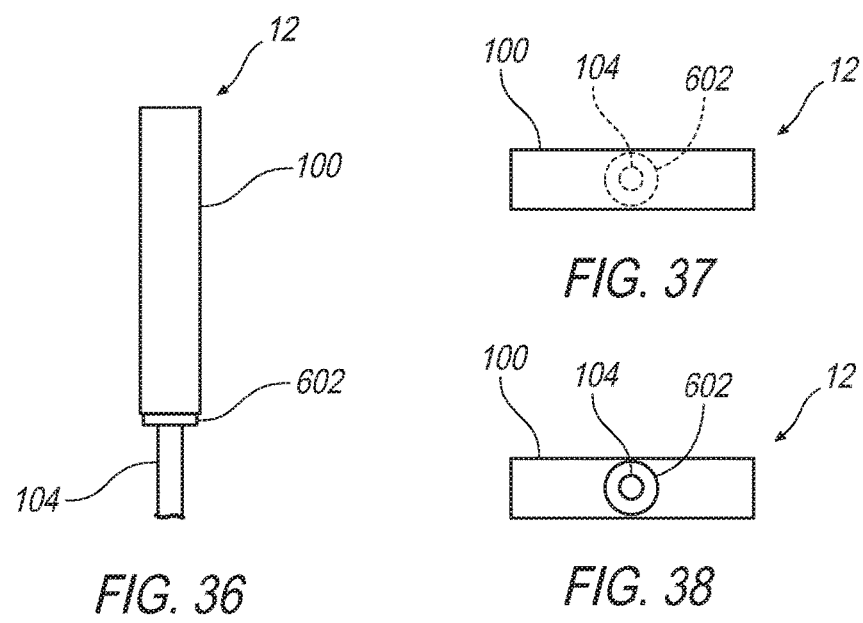

SALIVA MANAGEMENT SYSTEM

CROSS-REFERENCE TO RELATED APPLICATIONS

This is a continuation-in-part application that is based on and claims priority to U.S. Provisional Patent Application No. 62/913,444 filed on Oct. 10, 2019, U.S. Provisional Patent Application No. 62/783,562 filed on Dec. 21, 2018 and U.S. patent application Ser. No. 16/052,860 filed on Aug. 8, 2018, which are continuations-in-part of and claim priority to U.S. patent application Ser. No. 15/373,555 filed on Dec. 9, 2016, which claims the benefit of U.S. Provisional Patent Application No. 62/265,172 filed on Dec. 9, 2015, each of which is hereby incorporated by reference in its entirety.

BACKGROUND

Saliva production and removal is important to several biological functions including swallowing, digestion, and oral hygiene. For example, enzymes in saliva aid digestion. Saliva also hydrates the mouth and throat, aiding swallowing and promoting oral hygiene. Salivary glands may become impaired or damaged due to accident, trauma, illness, disease, and/or medical treatments including surgery, medications, radiation therapy, and chemotherapy treatments. In some cases, an accident, trauma, illness, disease, or medical treatment may seriously impair or permanently damage the salivary glands and, as a consequence, hinder or prevent normal salivary production.

Xerostomia is a condition that afflicts millions of people worldwide. Xerostomia is a condition in which saliva production is impaired or absent. Xerostomia may be caused by various diseases such as Sjogren's syndrome, human immunodeficiency virus (HIV), Alzheimer's disease, diabetes, cystic fibrosis, lupus, and rheumatoid arthritis. As another example, people undergoing cancer treatments such as radiation therapy and chemotherapy to the head and neck often experience a loss in saliva production, and the loss may be temporary or permanent. Medications may also diminish saliva production. Saliva production may also diminish as an individual ages and may become problematic at advanced ages.

With traditional systems, several problems may arise in a patient with compromised saliva production or removal. With no or limited ability to produce or remove saliva, an individual may not properly produce the enzymes necessary to properly digest food. Tooth decay, painful sores in the mouth, problems swallowing, and the inability to eat and speak may arise and may cause other significant health issues. For example, psychological stress and/or other problems may develop. At a minimum, an individual's quality of life may be negatively impacted.

Using traditional techniques, patients may also experience increased saliva production, swallowing inhibiting conditions, or a combination of these conditions. These conditions may lead to a buildup of saliva in a mouth of a patient. There is a need for improved procedures for fluid removal from the oral cavity. Accordingly, the systems and methods herein may be configured to assist in the addition or removal of fluid, such as saliva, from a mouth of a user such as a human or animal patient.

The present disclosure includes improved systems and methods to address the shortcomings of traditional systems. This includes improvements in replenishing and removing saliva, controlling saliva production, and delivery of medications to patients. Embodiments herein may provide improvements in comfort, versatility, operation, and appearance. Through the present disclosure, management of saliva disorders, patient compliance with therapies directed to saliva production and other health issues may be improved along with the patient's quality of life. Additionally, the improved systems and methods herein may make certain treatments, such as cancer treatments, more tolerable and provide for more stable and improved overall health.

BRIEF DESCRIPTION OF THE DRAWINGS

The present disclosure will become more fully understood from the detailed description and the accompanying drawings, wherein:

FIGS. 1A and 1B are perspective views of exemplary mouthpieces of the present disclosure;

FIG. 3 is an exploded view of embodiments of an exemplary mouthpiece, e.g., as shown in at least FIG. 2A;

FIGS. 10A, 10B, 10C and 10D illustrate embodiments of an upper saliva replenishment prosthesis of the present disclosure;

FIGS. 11A, 11B, 11C, 11D, 11E, 11F, 11G, 11H, 11I, 11J, and 11K illustrate embodiments of a saliva replenishment prosthesis of the present disclosure;

FIGS. 12A, 12B, 12C, 12D, 12E, and 12F illustrate embodiments of an exemplary over-the-tooth saliva replenishment prosthesis of the present disclosure;

FIGS. 13A, 13B, 13C, and 13D illustrate embodiments of an exemplary saliva replenishment prosthesis of the present disclosure;

FIG. 18 is a detail cross-sectional view of embodiments of a mouthpiece of the present disclosure, e.g., with a connection member;

FIG. 19 is a detail cross-sectional view of embodiments of a mouthpiece of the present disclosure, e.g., with a connection member;

FIG. 19A is a cross-sectional view of embodiments of a connection member and tube connection for a mouthpiece, e.g., in a connected or assembled condition;

FIGS. 35A, 35B, 35C and 35D illustrate front cross-section, first side cross-section, bottom, and second side cross-section views of an exemplary mouthpiece;

FIGS. 36, 37 and 38 illustrate side, top and bottom views of embodiments of an exemplary mouthpiece;

DETAILED DESCRIPTION

Figure 1A:
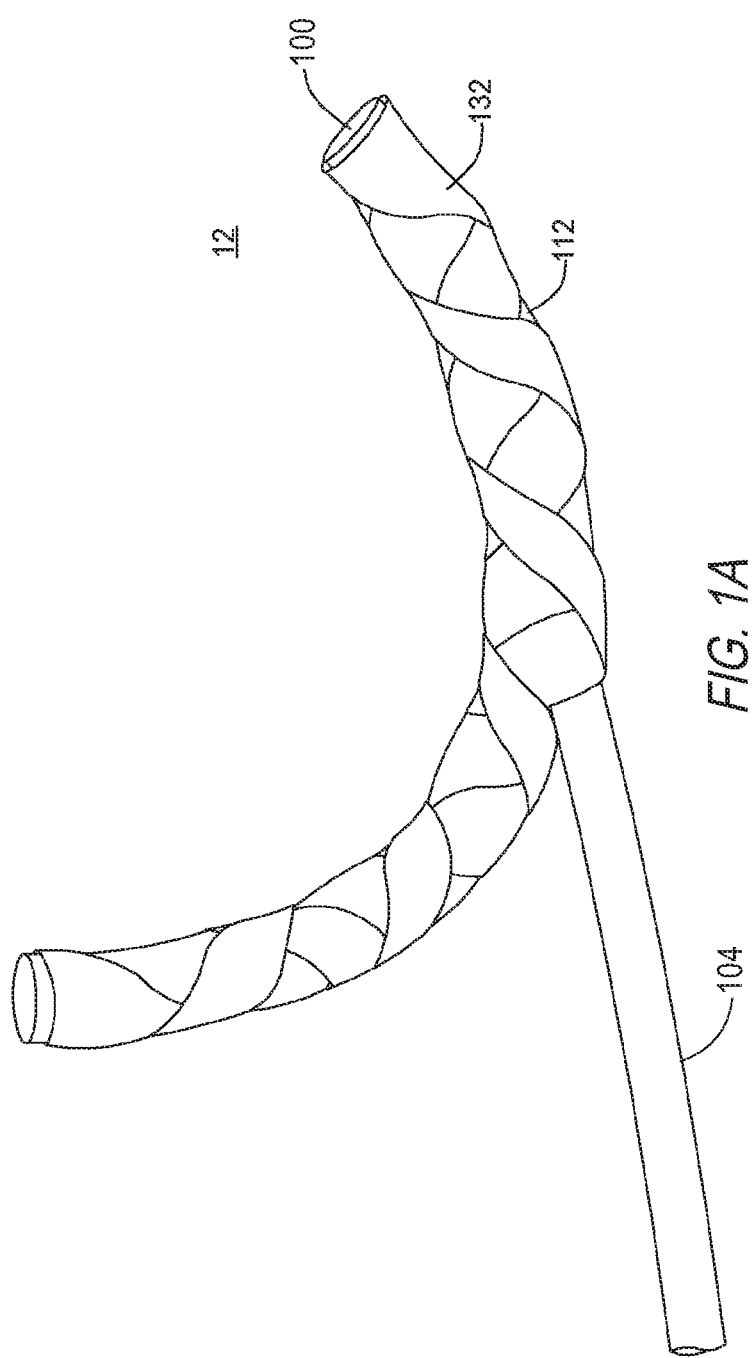
Figure 2A:
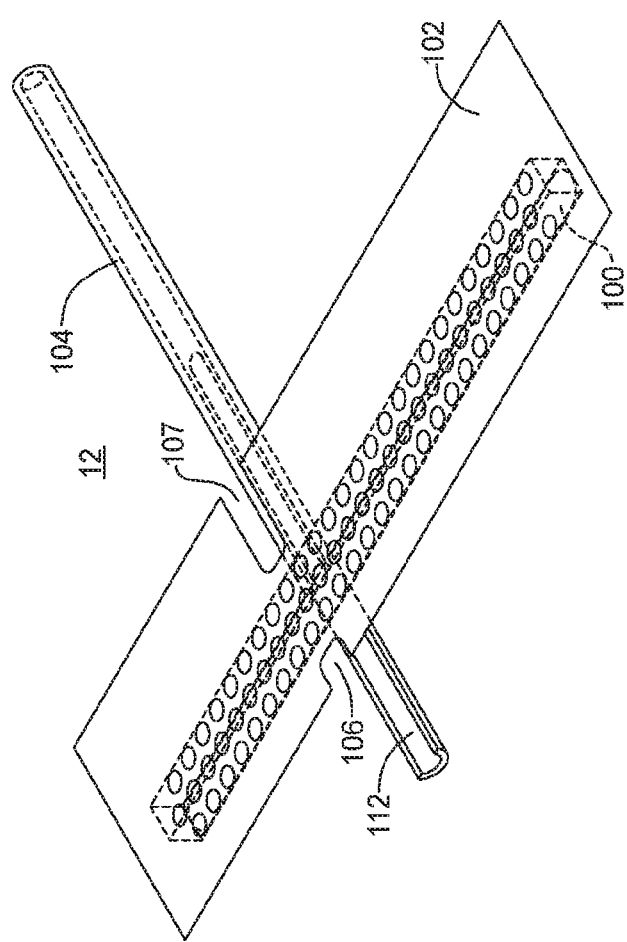
FIG. 2A is a perspective view of an exemplary mouthpiece of the present disclosure, e.g., in a flattened or opened configuration.
Figure 2B:
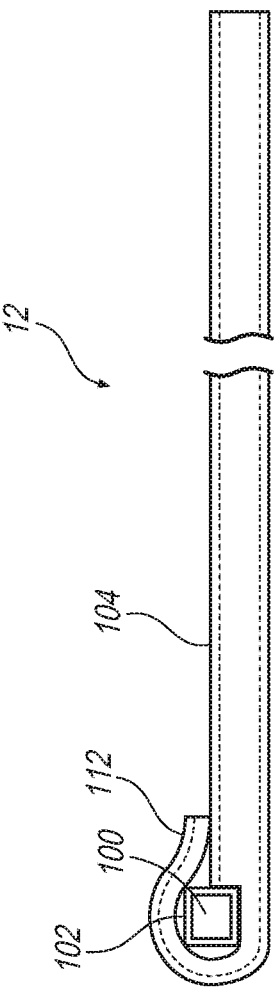
FIG. 2B is a side view of an exemplary mouthpiece in an assembled, wrapped or closed configuration, e.g., as shown in at least FIG. 2A.

The present disclosure relates to systems and methods for management and control of fluid, e.g., bodily fluids such as saliva, secretions or blood, or other fluids such as water, vitamins, moisture, agents, or medicine, or any combination thereof. Fluid management systems and methods may include a fluid transfer member (referred to herein as a "mouthpiece") configured to transfer fluid with respect to a body cavity including, e.g., the addition, removal, and circulation of fluid including liquid, gas, and solids particles. Transfer may include delivery, injection, irrigation, aspiration, or a combination thereof.

The systems and methods herein may be used for any medical procedure. This may include non-surgical and surgical procedures including open and minimally invasive surgery (MIS). Embodiments may be configured to manage fluids during dental, non-surgical, surgical, intensive care unit (ICU) or intubated procedures, open surgery, minimally invasive surgery (MIS), or a combination thereof.

A system may include a mouthpiece, a portable supply unit, a stationary unit, or a combination thereof. The portable supply unit may include a first fluid system, a first interface module, and a first control module. The stationary supply unit may include a second fluid system, a second interface module, and a second control module. The portable and stationary supply units may be configured to provide negative pressure, positive pressure, alternating pressure or a combination thereof.

The system may include a mouthpiece having one or multiple anchoring members, and may be used in combination with other mouthpieces. Anchoring members may be positioned in multiple locations in a body cavity, e.g., near or on any anterior, posterior, upper, or lower region of a mouth such as a gum line, submandibular glands, or a combination thereof. Anchoring members may include enhanced materials, structures, surface area and positioning to increase the transfer, wicking, removal and addition of any of the fluids described herein. For example, the mouthpiece may be configured with one or more anchoring members along a gum line of a mouth (e.g., gum line anchors or pads), on opposing sides of a mouth (e.g., cheek anchors or pads) or a combination thereof. The anchoring members may be configured to be placed closer to or over, a gum line of a mouth, a back or posterior area of the mouth, a front or anterior area of a mouth, or a combination thereof. The anchoring members may be positioned adjacent to, on or over a biting surface of a mouth, or a combination thereof. The anchoring members may be configured to be positioned near or directly over submandibular glands located near the back of the mouth. The anchoring member may be configured to provide optimized absorption for patients laying at a lower or higher angle, flat, incline or decline positions, or a combination thereof.

Each anchoring member may be connected to or include a fluid transfer conduit extending therefrom such as tubular member. The tubular members (e.g., tubes, tubing or tubing members) may be in fluid communication with a source such as a positive, negative or alternating pressure pump, e.g., directly connected to the source or joined by way of an interconnect (e.g., y- connector) in communication with a supply line of the source. Multi-anchor or multi-flow systems may be used in combination with cheek anchors, gum line anchors, other anchor systems, or a combination thereof.

A portable supply unit may be adapted to be carried by a user. The portable supply unit may include the first fluid system that is configured to fluidly couple to the mouthpiece to transfer (e.g., add, remove, or alternatingly add and remove) fluid with respect to the mouth via the mouthpiece, e.g., based on first operational settings. The first interface module may receive a first input and communicates the first operational settings. The first control module may selectively adjust the first operational settings based on the first input and second operational settings.

A stationary supply unit may include the second fluid system that is configured to fluidly couple to the mouthpiece to transfer (e.g., add, remove, or alternatingly add and remove) fluid with respect to the mouth via the mouthpiece, e.g., based on the second operational settings. The second interface module may receive a second input and communicate the second operational settings with the portable supply unit. The second control module may selectively adjust the second operational settings based on the second input and the first operational settings.

The mouthpiece may include a connection having a first end configured to be connected to a tubing and a second end configured to engage an anchoring member (e.g., foam member). The mouthpiece may include hydrophilic foam surrounded by a heat shrinkable layer. The mouthpiece may include or be surrounded by a heat shrinkable piece, and the hydrophilic foam may be connected to a tubular member. The mouthpiece may include only the hydrophilic foam without a co-extensive over-layer or surrounding layer. The foam may be connected to a tube. The present disclosure also provides methods related to the system and mouthpiece herein.

The anchoring member (e.g., hydrophilic foam) may be adapted to engage a lower dental arch adjacent a first tooth on a first side of a mouth, within the dental arch, adjacent a cheek, between an upper lip and an upper dental arch, or other appropriate areas within the mouth. The anchoring member (e.g., hydrophilic foam) may include a first passage extending between the vestibule on the first side of the mouth. One or more anchoring members may be adapted to engage the lower dental arch or a patient's lip. Anchoring members maybe configured to include or connect with first, second, and/or more tubular members. The first tubular member may extend within the mouth cavity proper from the anchoring member (e.g., hydrophilic foam) adjacent to an inner gum line. The second tubular member may extend within the vestibule on the first side of the mouth adjacent to an outer gum line. The second tubular member may include a first end fluidly coupled to the first passage and a second end extending outside of the mouth.

The first fluid system may be adapted to fluidly couple to the mouthpiece. The first fluid system may supply or remove saliva replenishment fluid to the mouth via the mouthpiece and/or remove fluid from the mouth via the mouthpiece based on first operational settings. The first interface module may receive a first input and may communicate the first operational settings with the stationary supply unit. The first control module may selectively adjust the first operational settings based on the first input and second operational settings communicated by the stationary supply unit.

The stationary supply unit may include a second fluid system, a second interface module, and a second control module. The second fluid system may be adapted to fluidly couple to the mouthpiece. The second fluid system may supply saliva replenishment fluid to the mouth via the mouthpiece or remove fluid from the mouth via the mouthpiece based on the second operational settings. The second interface module may receive a second input and may communicate the second operational settings with the portable supply unit. The second control module may selectively adjust the second operational settings based on the second input and the first operational settings.

Further areas of applicability of the present disclosure will become apparent from the detailed description provided hereinafter. It should be understood that the detailed description and specific examples are intended for purposes of illustration only and are not intended to limit the scope of the disclosure.

The present disclosure provides a mouthpiece that may be placed and attached to a lower portion of a mouth and may be used to replenish or remove and/or control saliva in a patient or user. The mouthpiece may further be placed in an upper portion of a mouth and/or both an upper and lower portion of the mouth. The user may be a male or female human, an adult or child, or any animal. The mouthpiece may be used during treatment of temporary conditions such as a temporary loss of swallowing capability due to a stroke or trauma, or chronic conditions and diseases such as Xerostomia and cancers affecting salivary function.

The mouthpiece may be used to supply and/or remove fluid from the mouth. The mouthpiece is designed so that it may be relatively inconspicuous and minimally intrusive, and may be continuously worn for prolonged periods, (e.g. about 2 hours to about 8 hours, including about 6 hours) for example days and weeks. The mouthpiece is further designed so that it may be used to supply a saliva replenishment fluid in a manner that mimics a normal saliva flow within the mouth. By incorporating the features disclosed herein, the mouthpiece may be comfortably used without compromising chewing, eating, speaking, and sleeping, and may promote patient compliance with therapies dependent on the use of the mouthpiece.

The mouthpiece may be patient-specific, e.g., individually sized and made to fit a particular user. The mouthpiece may have a modular construction that further enables components of the mouthpiece as produced to be altered and custom fit to a particular patient. The mouthpiece may include structures based on or corresponding to imaging or scans of the particular patent. The modular construction may also enable one or more components of the mouthpiece to be individually replaced without the need for another complete replacement mouthpiece. The components may be individually replaced to maintain a desired sanitary condition of the mouthpiece.

FIGS. 1A-48 illustrate exemplary embodiments including devices, systems and methods of the present disclosure. Embodiments may include one or more mouthpieces 12 according to the present disclosure. All or any portions of the systems herein may include medical-grade, antibacterial, non-latex/latex free, disposable, or low waste materials or a combination thereof.

As shown in FIGS. 7-13, mouthpiece 12 may be positioned and anchored relative to any portion of a body such as a bodily cavity. Mouthpiece 12 may be positioned in any bodily cavity such as a mouth cavity. Mouthpiece 12 may be anchored adjacent lower teeth 20 in a lower jaw bone by gingiva or gum. The lower dental arch includes alveolar processes that receive roots of the lower teeth, the lower teeth, and portions of the gum covering the alveolar processes and surrounding the lower teeth. The lower teeth generally include about 12 deciduous teeth in a child and about 16 permanent teeth in an adult.

Figure 7B:
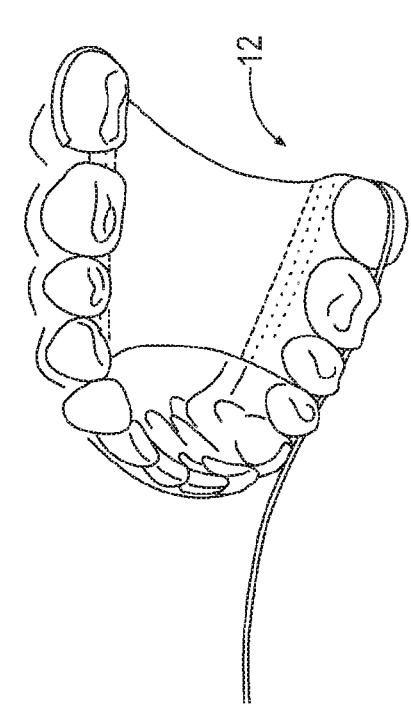
FIGS. 7A, 7B, 7C, and 7D illustrate embodiments of an upper and lower saliva prosthesis of the present disclosure.
Figure 7D:
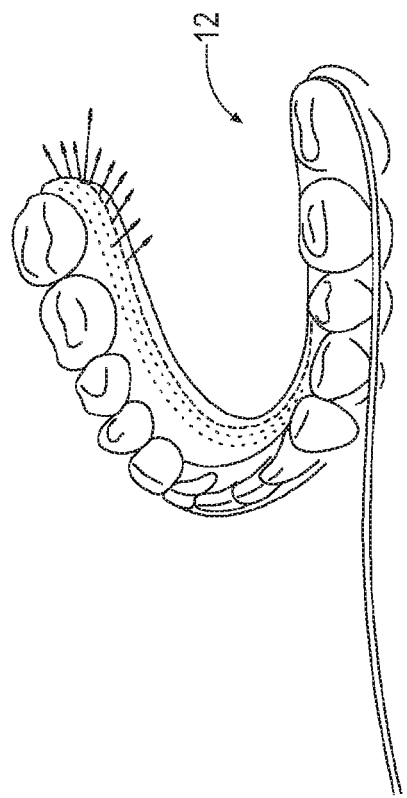
Figure 7A:
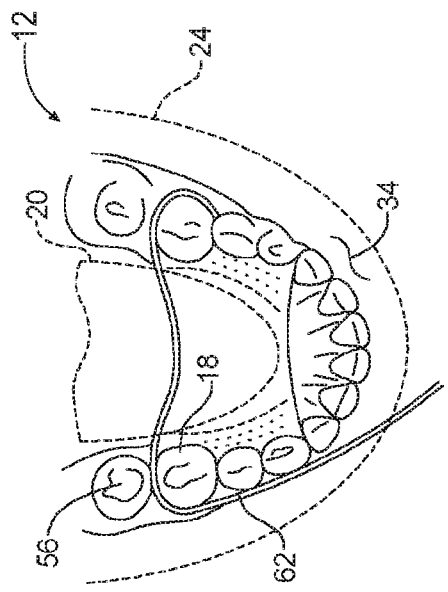
Figure 7C:
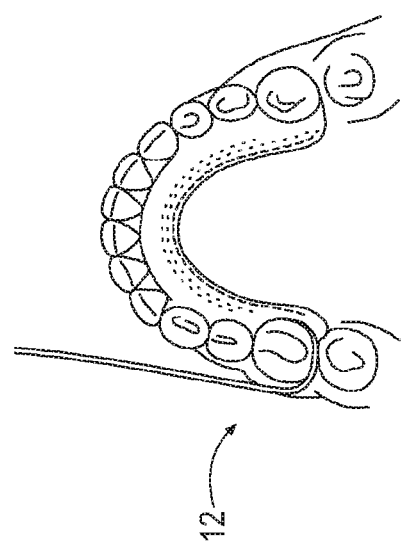

For exemplary purposes, as illustrated in FIG. 7A, the lower teeth presented include 14 teeth: four incisors, two canines, four premolars, and four molars. The lower teeth include lingual surfaces 18 facing the mouth cavity proper and a tongue 20 (shown in phantom), labial or buccal surfaces 62 facing the vestibule 34 and a cheek 24 (shown in phantom) and lips, and surfaces of contact between adjoining teeth. The lower teeth further include crowns facing upper teeth of an upper jaw bone and defining a lower bite surface or plane. Together, the lower teeth and the gum define an inner gum line and an outer gum line. The mouth includes salivary glands comprising the sublingual gland in the anterior or front area of the mouth (e.g., covering the mouth floor), the submandibular gland in the medial or central area of the mouth (e.g., under the tongue), and the parotid glands in each side of the posterior or back areas of the mouth (e.g., adjacent the cheeks). The parotid glands lead to parotid ducts, referred to as Stensen ducts. The submandibular glands lead to submandibular ducts, referred to as submaxillary or Wharton's ducts. All or any portion of the systems herein may be positioned and/or anchored relative to any bodily portion such as those discussed herein.

Referring to FIGS. 1A-48, the mouthpiece 12 may include a first anchoring member 100 including foam, a second member 102 annularly disposed about the first anchoring member 100, and a first tubular member 104 partially disposed within the first anchoring member 100 and supported by the second anchoring member 102. The first and second anchoring members 100 and 102 may be sized to fit within the spaces between the lower lip and the lower teeth, with the first tubular member protruding from the mouth to provide vacuum or saliva substitute to the mouth. The mouthpiece may include a deformable first anchoring member 100 may be generally solid structures and may have various shapes adapted to fit within the spaces adjacent to the molars and adjoining teeth of the lower teeth.

With reference to FIGS. 2A, 2B, 3, 4A and 4B as examples, the mouthpiece 12 may include the first anchoring member 100 (e.g., including foam or hydrophilic foam), the second anchoring member 102 (e.g., including foam or hydrophilic foam and shown as a tube in a flat or closed configuration), and the first tubular member 104. The anchoring member 100 may be configured to extend about the lower gum. The anchoring member 100 may have a generally tapered polyhedral shape as illustrated, or may have a contoured shape resembling a natural tooth that may otherwise reside in the space.

The anchoring member may be any appropriate foam material. In various embodiments, the anchoring member 100 is open cell foam. The anchoring member 100 may be a medical-grade polyurethane, hydrophilic foam, e.g., a hydrasorb foam material. Anchoring member 100 may include a base material of polyether polyisocynate resins. Anchoring member 100 may be sterilizable and/or sterilized. Anchoring member 100 may be die cut from sheets have a uniform thickness, and/or be molded to a selected shape. For example, anchoring member 100 may be made from 18"× 36" sheets of a selected thickness, such as about 1 centimeter (cm) to about 3 cm.

Any or all of the components herein such as anchoring member 100 may have any combination of material properties that provide the structures, functions and improvements as described herein. Anchoring member 100 may have properties such as: Hydrophilic Absorption Capacity (Water): up to 15× Dry Wt. [ASTM D1667]; Cell Structure (DRY Avg.): 86 Cells/Linear In; Density (Nominal/DRY): 7.5 lb/ft3 [ASTM D3574]; Elongation % (DRY Avg.): 650% [ASTM D3574]; Expansion in Water (length)(Avg.): 31% (Avg.) [ASTM F1087]; Foam Moisture Content (DRY Avg.): 3.56% [Karl Fischer Method]; Indention Force Deflection (IDF): [ASTM D3574 Test B1] IDF @ 25%: (N) 133% IDF @ 65%: (N) 346%; Resiliency/Rebound Test (RT [ASTM D3574 Test B1] RT @ 25%: (N) 121%; Compression Set (DRY Avg.): [ASTM D3574] 25%: 16.0% 50%: 36.0%; and Tensile Strength (Dry): 30.0 lbf/In2 [ASTM D3574 Test B1].

Figure 4A:
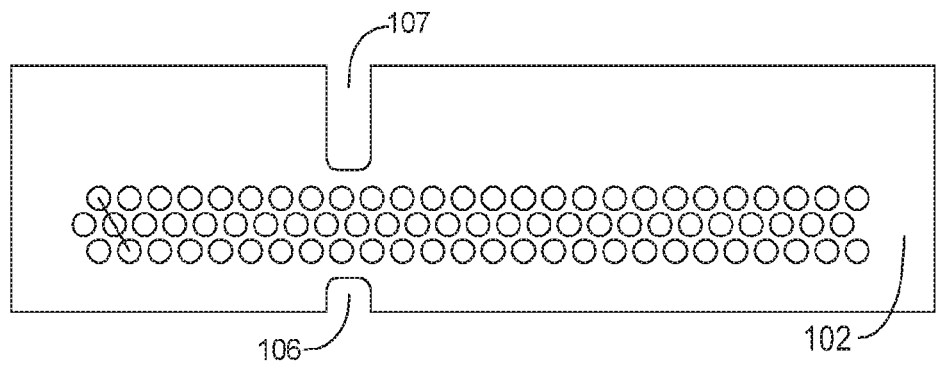
FIG. 4A is a top view of embodiments of an exemplary tube of a mouthpiece, e.g., as shown in at least FIGS. 1A-3.
Figure 4B:
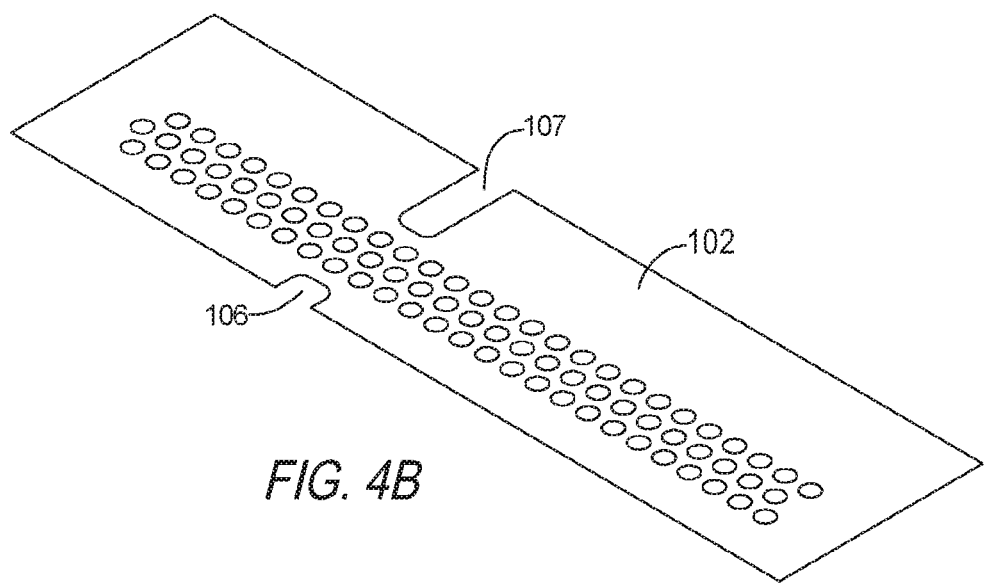
FIG. 4B illustrates embodiments of an exemplary tube of a mouthpiece, e.g., as shown in at least FIGS. 1A-3.

As shown in FIGS. 4A and 4B, the anchoring tube 122 and/or capture portion 112 may be perforated to accept saliva from the mouth or saliva replacement tubular member 104. The size and shapes of these perforations may vary. In a flattened configuration, a notch or pair of notches 106, 107 may be utilized to be positioned about the tubular member 104 and the hydrophilic foam 102.

The front surface 132 may be adapted and disposed to engage one or more of the surface of contact, the lingual surface, and the buccal surface of the molar. The front surface 132 may be further disposed to allow one end of the tubular member 104 to exit the front surface 132 adjacent the lingual surface of the molar and an opposite end of the passage to exit the front surface adjacent the buccal surface of the molar. In this way, the front surface 132 may be disposed to allow the first tubular member 104 to extend from the front surface 132 adjacent the lingual surface of the molar, and the second tubular member to extend from the front surface adjacent the buccal surface 62 of the molar. The front surface 132 may be generally flat as illustrated by the present example and, optionally, may include a portion complementary to the adjoining surface of contact of the molar. In this way, the front surface may engage and thereby resist relative movement between the first anchoring member 100 and the molar 56.

The first and second anchoring members 100 and 102 may be made in a mirror image to that described herein. In this way, the mouthpiece 12 may be configured so that the tubular member 104 exits the mouth 10 on the left side of the user.

The first and second anchoring members 100 and 102 may be attached in any suitable manner. For example, a suitable adhesive such as an adhesive that adheres dentures to a gum may be used. The first and second anchoring members 100 and 102 may be attached in a semi-permanent manner using a bone fastener. The first and second anchoring members 100 and 102 may be made from any suitable dental material which allows saliva infiltration. Suitable dental materials include, but are not limited to, biocompatible polymers such as acrylic materials, and metals such as titanium.

Figure 5:
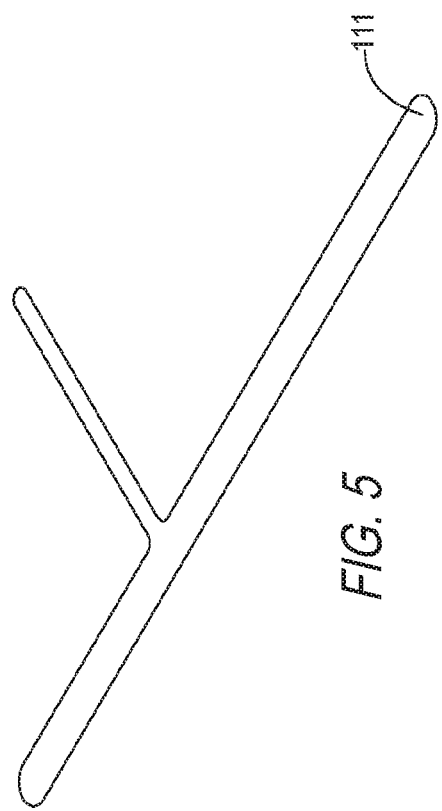
FIG. 5 illustrates embodiments of an exemplary stiffening member of a mouthpiece, e.g., as shown in at least FIGS. 1A-3.

FIG. 5 represents a metal deformable support member 111 which may be part of or inserted adjacent to the anchoring member 100 (e.g., hydrophilic foam), as illustrated in FIGS. 1B and 3. This metal deformable support member may then be used to form the mouthpiece prior to insertion between the lip and gum adjacent to the lower teeth.

Figure 6B:
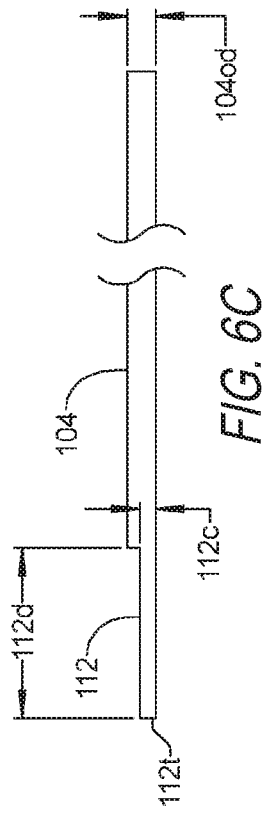
FIGS. 6A, 6B, and 6C illustrate embodiments of a tube member associated with the mouthpiece of the present disclosure.
Figure 6C:
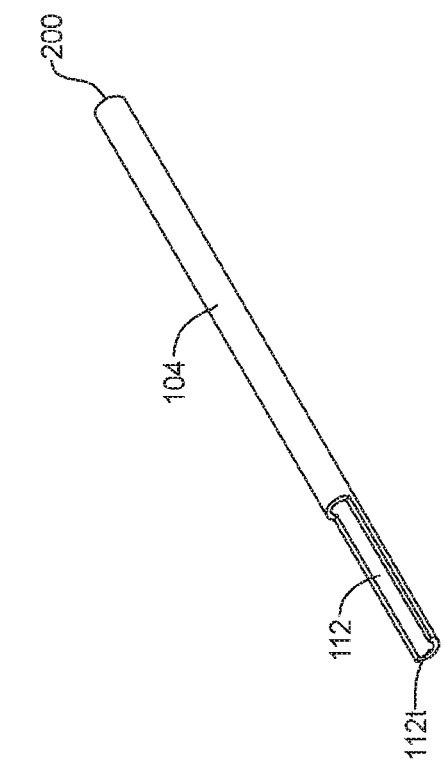
Figure 6A:
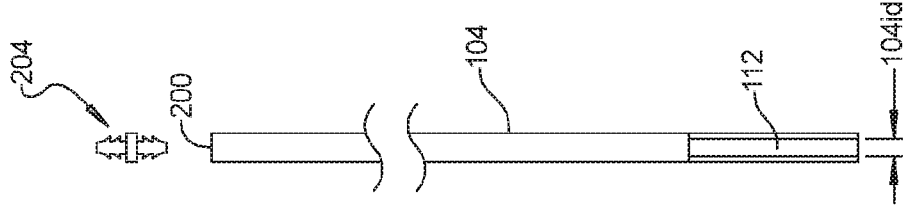

FIGS. 6A-6C represent tubular member 104 placed adjacent to the anchoring member 100 (e.g., hydrophilic foam) and within the heat shrink material of tube 102. A portion of the tubular member 104 may be passed though the slots 106 and 107. The tubular member 104 has a first or engagement including a capture or annular portion 112, e.g., interchangeably referred to as annular portion 112. Capture or annular portion 112 may be is perforated, notched, and/or annularly disposed about hydrophilic foam 110. Capture or annular portion 112 may be configured to allow suction to be applied to the open pore hydrophilic foam 100.

FIGS. 7A-7D represent an exemplary upper and lower saliva replenishment prosthesis of the present disclosure. The upper and lower prosthesis are made of materials having a soft durometer. Embodiments may include an inner passage and a plurality of apertures that link an outer surface of the prostheses with the inner aperture. As shown, each prosthesis utilizes an outer supply or extraction tube that may be coupled to a fluid supply or a vacuum as described herein.

Figure 8:
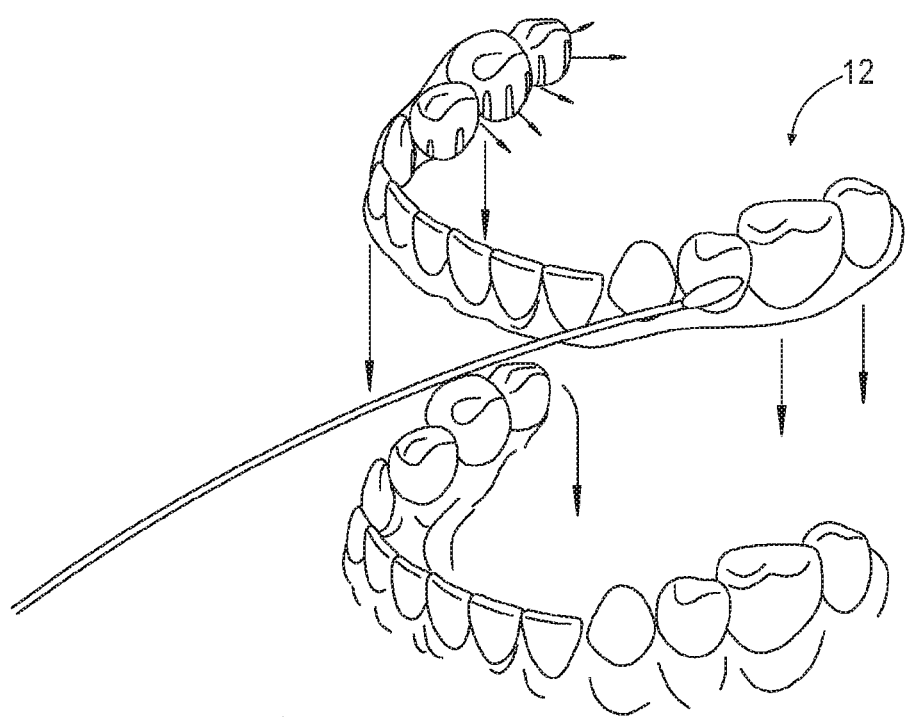
FIG. 8 illustrates embodiments of an installation of a lower mouth prosthetic of the present disclosure.

FIG. 8 represents the installation of a lower mouth prosthetic of the present disclosure. Shown is a film layer, which is coupled to the teeth using a water soluble adhesive. The fluid extraction tube is placed along the outside of the tooth ridge. Should a vacuum be drawn through the tube, fluid is drawn through apertures defined through the polymer layer. This configuration may be used as both the upper and lower prosthesis are made of materials having a soft durometer. Embodiments may include one or more inner passages between the teeth that may be used to draw out saliva. The plurality of apertures may link an outer surface of the prostheses with the inner aperture. As shown, each prosthesis utilizes an outer supply or extraction tube that may be coupled to a fluid supply or a vacuum as described herein.

Figure 9A:
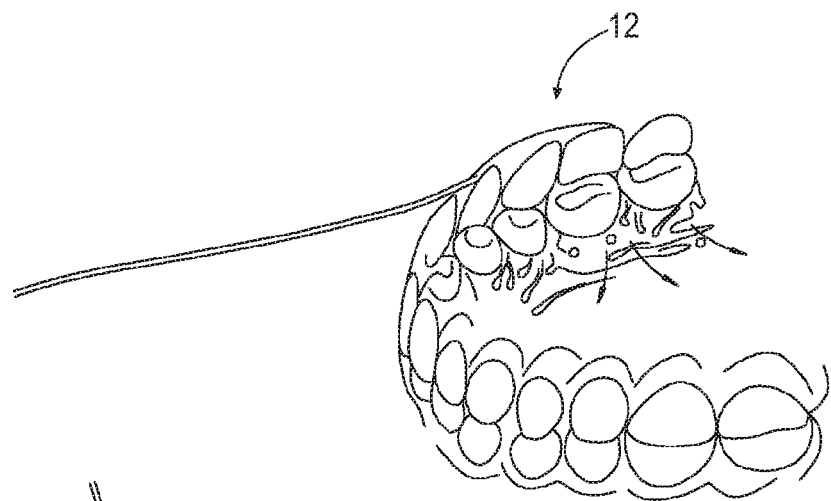
FIGS. 9A, 9B and 9C illustrate embodiments of an upper saliva prosthesis of the present disclosure.
Figure 9B:
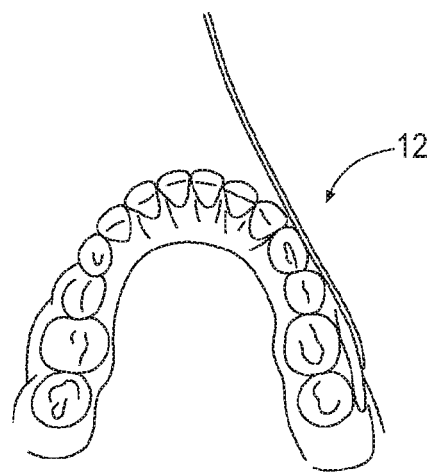
Figure 9C:
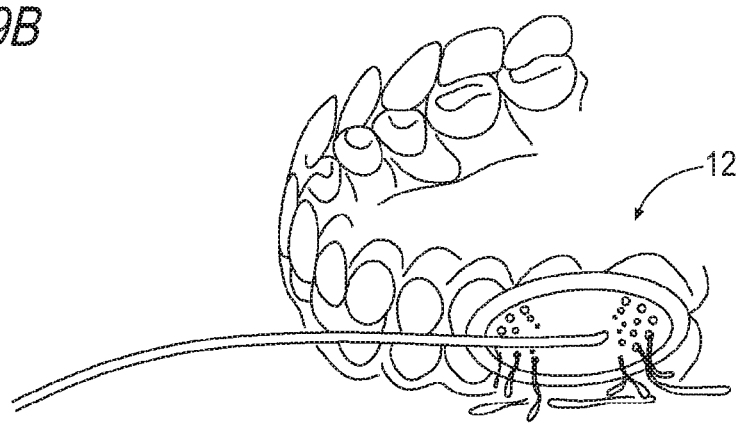
Figure 11I:
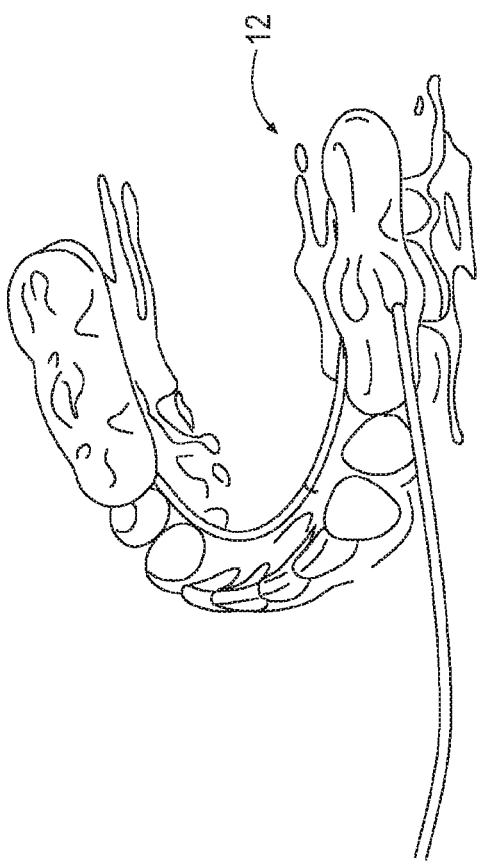
Figure 11K:
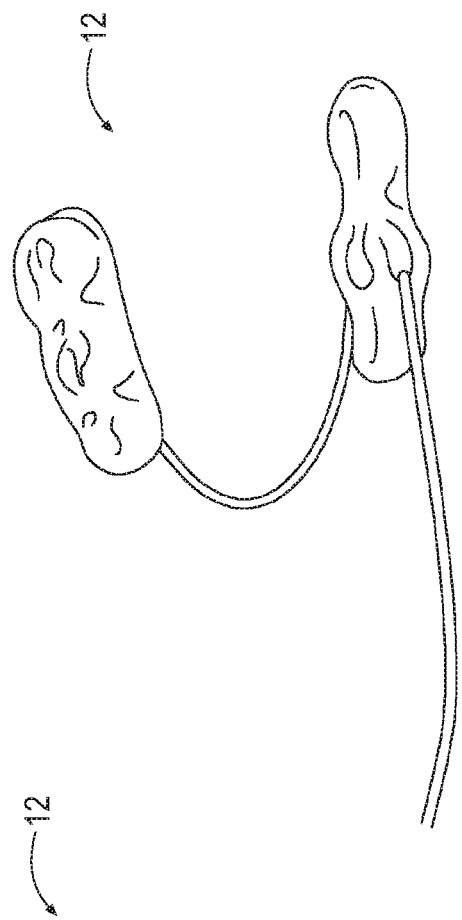
Figure 11J:
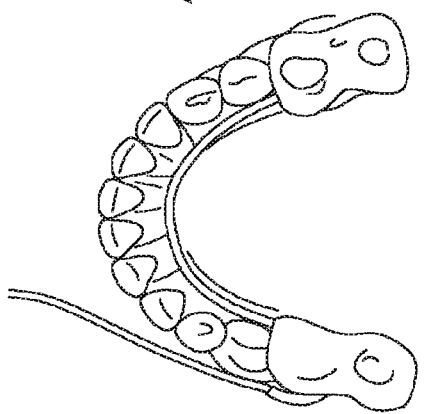
Figure 12A:
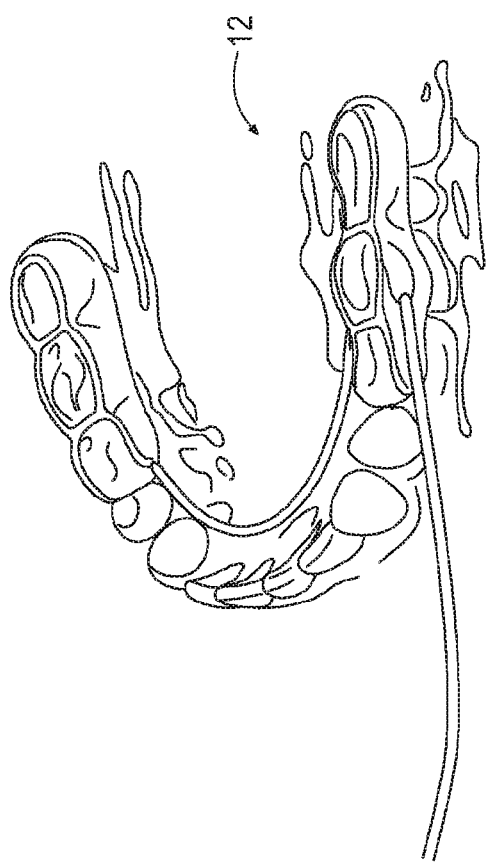
Figure 12C:
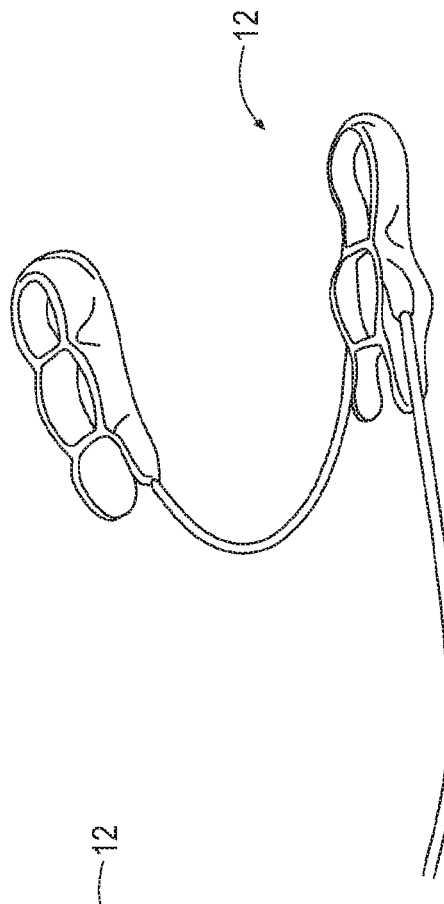
Figure 12B:
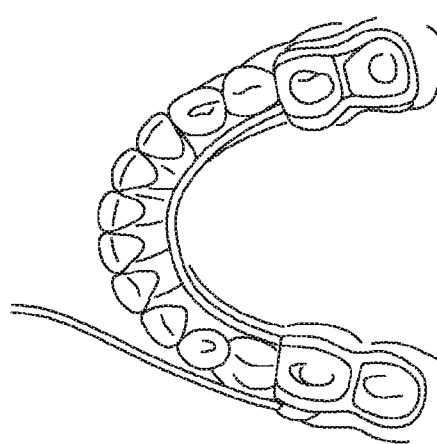

FIGS. 9A-9C represent an exemplary upper saliva replenishment and/or removal prosthesis of the present disclosure. As is shown, a deformable polymer material has a fluid transport tube disposed therethrough. The deformable member is generally oval and is configured to be fixed to the molars between the tooth and the gum line. The device has a through passage and a plurality of excretion or vacuum holes. The fluid extraction tube is placed along the outside of the tooth ridge. Should a vacuum be drawn through the tube, fluid is drawn through apertures defined through the polymer layer. This configuration may be used as both the upper and lower prosthesis are made of materials having a soft durometer. Embodiments may include one or more inner passages between the teeth that may be used to draw out saliva. The plurality of apertures link an outer surface of the prostheses with the inner aperture. As shown, each prosthesis utilizes an outer supply or extraction tube that may be coupled to a fluid supply or a vacuum as described herein.

FIGS. 10A-10D represent an exemplary saliva replenishment or removal prosthesis of the present disclosure. The fluid extraction tube is placed along the outside of the tooth ridge. The material that forms the saliva replenishment or removal prosthesis is plastically deformable and includes a plurality of through passages that remain open upon disposition over the teeth. The passages remain open because they have a surface that resists the sticking of one inner aperture surface to another. They are also configured to be strong enough not to collapse of the application of the vacuum. Should a vacuum be drawn through the tube, fluid is drawn through apertures defined through the polymer material. This configuration may be used as both the upper and lower prosthesis are made of materials having a soft durometer. Embodiments may include one or more inner passages between the teeth that may be used to draw out saliva. The plurality of apertures link an outer surface of the prostheses with the inner aperture. Each prosthesis may utilize an outer supply or extraction tube that may be coupled to a fluid supply or a vacuum as described herein.

FIGS. 11A-11J represent a saliva replenishment and/or removal prosthesis of the present disclosure. As is shown, a deformable polymer material has a fluid transport tube disposed therethrough. The deformable member is generally oval and is configured to be fixed to the molars between the tooth and the gum line. The device has a through passage and a plurality of excretion or vacuum holes. The fluid extraction tube is placed along the outside of the tooth ridge. Should a vacuum be drawn through the tube, fluid is drawn through apertures defined through the polymer layer. This configuration may be used as both the upper and lower prosthesis are made of materials having a soft durometer. Embodiments may include one or more inner passages between the teeth that may be used to draw out saliva. The plurality of apertures link an outer surface of the prostheses with the inner aperture. As shown, each prosthesis utilizes an outer supply or extraction tube that may be coupled to a fluid supply or a vacuum as described herein.

FIGS. 12A-12F represent an exemplary saliva replenishment and/or removal prosthesis of the present disclosure. The prosthetic member is formed around the molars and do not interfere with the molar bite surface. As with FIGS. 7A-7D, exemplary upper and lower saliva replenishment and/or removal prosthesis of the present disclosure. As shown the prosthesis travels over the molar region and is positioned under the tongue at only a single location. The upper and lower prosthesis are made of materials having a soft durometer. Embodiments may include an inner passage and a plurality of apertures that link an outer surface of the prostheses with the inner aperture. As shown, each prosthesis utilizes an outer supply or extraction tube that may be coupled to a fluid supply or a vacuum as described herein.

FIGS. 13A-13D represent an over the tooth saliva replenishment and/or removal prosthesis of the present disclosure. As with FIGS. 7A-7D, exemplary upper and lower saliva replenishment prosthesis of the present disclosure. As shown the prosthesis travels over the molar region and is positioned under the tongue at only a single location. The upper and lower prosthesis are made of materials having a soft durometer. Embodiments may include an inner passage and a plurality of apertures that link an outer surface of the prostheses with the inner aperture. As shown, each prosthesis utilizes an outer supply or extraction tube that may be coupled to a fluid supply or a vacuum as described herein.

The first and second anchoring members may be non-custom, semi-custom components, custom or patient-specific components. As used herein, non-custom components may refer to components made without features based on a particular user. Semi-custom components may refer to components made in advance that include a majority of predetermined features not based on a particular user and at least one feature based on a particular user. Custom components may refer to components specifically made for a particular user. The patient-specific components may include semi-custom or custom components, e.g., formed based on a particular user's lower dental arch and surrounding mouth anatomy using various techniques such as dental impressioning, scanning and direct and indirect visualization techniques.

Any or all of the components herein such as anchoring member 100 may be a medical-grade polyurethane, hydrophilic foam, e.g., a hydrasorb foam material. This foam may include a base material of polyether polyisocynate resins. Anchoring member 100 may be sterilized and/or is sterilizable, and may be die cut, molded to a shape or a combination thereof. For example, anchoring member 100 may be made from 18"×36" sheets (⅛" to ¾" wetted thickness). Hydrophilic Absorption Capacity (Water): up to 15× Dry Wt. [ASTM D1667] Cell Structure (DRY Avg.): 86 Cells/Linear In. Density (Nominal/DRY): 7.5 lb/ft3 [ASTM D3574] Elongation % (DRY Avg.): 650% [ASTM D3574] Expansion in Water (length)(Avg.): 31% (Avg.) [ASTM F1087] Foam Moisture Content (DRY Avg.):. 3.56% [Karl Fischer Method] Indention Force Deflection (IDF): [ASTM D3574 Test B1] IDF @ 25%: (N) 133% IDF @ 65%: (N) 346% Resiliency/Rebound Test (RT [ASTM D3574 Test B1] RT @ 25%: (N) 121% Compression Set (DRY Avg.): [ASTM D3574] 25%: 16.0% 50%: 36.0% Tensile Strength (Dry): 30.0 lbf/In2 [ASTM D3574 Test B1].

Returning reference to FIGS. 6A, 6B, and 6C, mouthpiece 12 may include tubular member 104. The tubular member 104 may include a selected length and include a first terminal end 200 that may be connected to a connector 204 such as a barb connector. The tubular member 104 may be any appropriate tube, as discussed herein. The tube may be medical grade and/or include a composition (e.g. antibacterial medical grade material) for extended and non-toxic use in an oral cavity of the user. The tubular member 104, in various embodiments, may include tygon tubing of ND 100-65 material having selected characteristics such as having or being made from a biocompatible non-DEHP polymer material. The tubular member 104 may have further various characteristics, as discussed herein.

The barb connector 204 may fit into the terminal end 200 and allow for the tubular member 104 to be connected to a selected system. As discussed above, the tubular member 104 may be connected to source tubing 105 in communication with source 107 or directly to source 107. Source 107 may be configured to provide positive pressure (e.g., injection), negative pressure (e.g., suction or vacuum), or alternating pressure (e.g., a combination thereof). The source 107 may include a portable pump, a fixed pump, or a fixed source of a vacuum. In various embodiments, the source 107 may include a hospital vacuum system that may include a whole hospital vacuum, suction systems used in dental offices, etc. The tubular member 104 may allow for connection of the mouthpiece 12 from the selected user and to the source 107 for adding or removing fluid from a user, e.g., injecting or withdrawing moisture, medicine, agents, saliva or a combination thereof. Given the length of the tubular member 104, it may be able to move freely and selectively even while the mouthpiece 12 is in place. The tubular member 104 may also be used to deliver a saliva replacement through the mouthpiece 12 to the user.

The tubular member 104 may include a cut or notched region 112. The cut or notched region may include a portion, such as about one-half, of the tubular member 104 removed from the tubular member 104 over a selected distance 112$d$, such as about 5 millimeters (mm) to about 50 mm, including about 25 mm, from the tubular member 104. The tubular member 104 may include an external diameter or outer diameter 104$od$ and an internal diameter 104$id$. The external diameter 104$od$ may be about 2.0 mm to about 0.1 mm, including about 0.2 mm to about 0.1 mm, and further including about 0.19 mm. The internal diameter 104$id$ may be about 1.5 mm to about 0.01 mm, including about 0.5 mm to about 0.1 mm, and further including about 0.13 mm. At the cut portion 112, a dimension 112$c$ from the external surface to an edge of the cut wall may be about 0.1 mm. The length of the tube, the internal diameter of the tube, and other dimensions may be selected based upon the amount of material to be removed and/or delivered through the mouthpiece 12, the vacuum force and/or flow force of the material through the tubular member 104, or other factors.

The tubular member 104 may have properties such that at the noted dimensions it will not collapse with selected pulsations. As discussed herein, the mouthpiece may be placed in a patient's mouth and a pulse of vacuum and/or fluid delivery may occur through the tube. Thus, the tubular member 104 will not collapse under the negative pressure within the tubular member 104 due to suction, especially pulsatile suction therethrough.

Figure 14A:
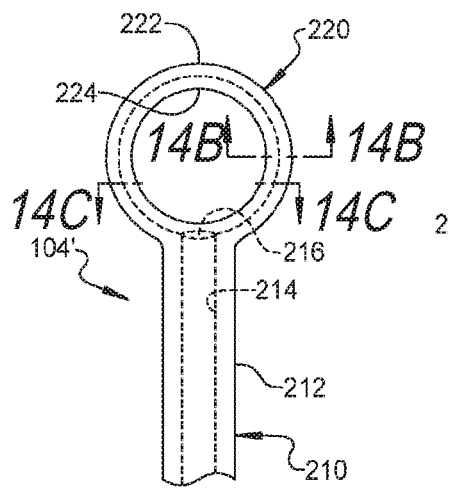
FIG. 14A illustrates embodiments of an exemplary tube member associated with the mouthpiece of the present disclosure.
Figure 14B:
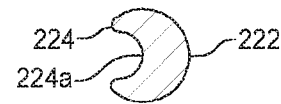
FIGS. 14B and 14C are cross-sectional views of embodiments of an exemplary capture portion of a mouthpiece, e.g., as illustrated in at least FIG. 14A.

With reference to FIGS. 14A-B, mouthpiece 12 may include tubular member 104, e.g., configured as tubular member 104'. The tubular member 104' may be formed as a single member without a cut portion, in other words without the notch 112. The tubular member 104' includes an elongated portion 210 that includes an external wall 212 and defines an internal cannula 214. The tubular member 104' may terminate or have the internal cannula 214 terminate at an opening 216. The tubular member 104' may further include a terminal end 200' similar to the end 200 of the tubular member 104.

Near or formed around the terminal opening 216 is a loop or integral loop or hoop 220, also referred to as a capture or annular portion 220 or 112. The hoop 220 may include an external surface or wall 222 and an internal surface or wall 224. With additional reference to FIGS. 14B-C, the internal surface may be formed to include a depression or groove 224$a$ around all or a portion of the hoop 220. The groove 224$a$ may be in communication with the terminal opening 216. Thus, a suction or fluid delivery may be made through the passage 214 and to the groove 224$a$. The hoop 220, including the groove 224$a$, may be molded to and/or with the tubular member 104'. The tubular member 104' may be formed as one integral piece including the elongated portion 210 and the hoop 220.

In various embodiments, the tubular member 104' may be similar to a sewing needle where the shaft of the needle is hollow to form the cannula 214 and the eye of the needle is the molded portion 220. The tubular member 104', however, may be formed of the similar or identical material to the tubular member 104. The tubular member 104' may include or be formed from tygon tubing of ND 100-65 material and may be molded to include the selected hoop 220.

Figure 15A:
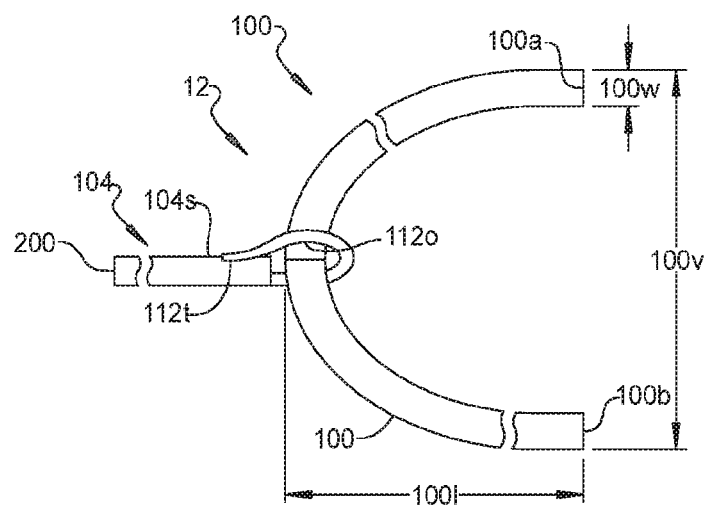
FIGS. 15A and 15B illustrate embodiments of an exemplary mouthpiece assembly with a tube member, e.g., as illustrated in at least FIGS. 6A-6C.
Figure 15B:
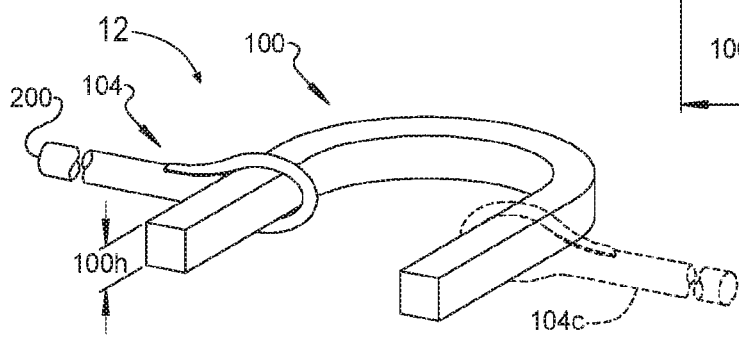
Figure 16:
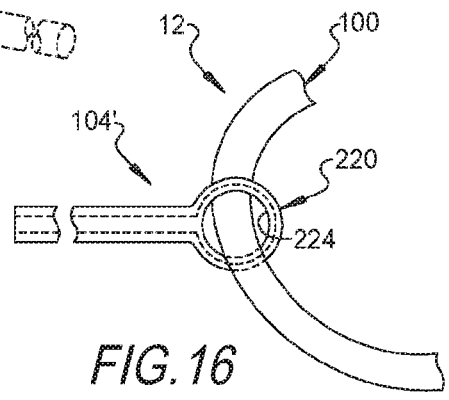
FIG. 16 illustrates embodiments of an exemplary mouthpiece with a tube member, as illustrated in at least FIG. 14A.

With continuing reference to FIGS. 6A-6C and FIG. 14A, the tubular member 104, 104' may be connected to the anchoring member 100 (e.g., foam 100) to form the mouthpiece 12, as illustrated in FIG. 15A, FIG. 15B, and FIG. 16. In FIG. 15A and FIG. 15B the tubular member 104, as illustrated in FIGS. 6A-6C, is formed so that the notched or annular portion 112 is folded upon an outer wall or surface 104$s$ of the tubular member 104. A terminal end portion 112$t$ may be folded toward the terminal end 200 and placed on the outer surface 104$s$ of the tubular member 104. The terminal end 112$t$ may be fixed to the outer surface 104$s$ in any appropriate manner, such as with an adhesive, a physical member (e.g. a zip tie or shrink tube), or other appropriate fixation. In various embodiments the terminal end 112$t$ is adhered to the outer surface 104$s$ with a medical grade adhesive such as type 4011, medical device instant adhesive. Any appropriate amount of the notched or annular portion 112 may be fixed to the outer surface 104$s$ and not simply at the immediate terminal end, but may extend a selected distance such as about 1mm, about 2mm, or an appropriate length from the terminal end 112$t$ to allow for appropriate adhesion of the notched portion to the outer surface 104$s$ of the tubular member 104. The anchoring member 100 is positioned through the loop or opening 112$o$. The foam 100 may be pulled through the opening 112$o$ or the cut portion

112 may be folded over the anchoring member 100 during assembly and production of the mouthpiece 12.

Tubular member 104, e.g., the notched or annular portion 112, may be annularly disposed about and move along anchoring member 100. Tubular member 104 may be configured to rotate and slide along anchoring member 100, e.g., to minimize skin irritation and breakdown on and near the lips. Notched or annular portion 112 include a non-fixed, non-permanent, slideable, and/or modular connection with anchoring member 100. Tube 105 may be completely wrapped around a transverse perimeter of anchoring member 100, e.g., to provide positive, negative or alternating pressure around an entirety of the transverse perimeter.

As illustrated in FIG. 15A and FIG. 15B, the mouthpiece 12 may be formed of only the tubular member 104 and the foam 100. The foam 100 may be formed of a selected material such as an open cell foam configured for the structures and functions disclosed herein. The foam 100 may be formed into a selected specific shape, such as generally C-shaped or semi-circular such as by di-cutting or cutting the foam material into a selected arc shape to allow it to substantially shaped, mold, or be fitted to the buccal surface 62 of the dental arch in the user and substantially along and on the gum line of the user. Accordingly, the mouthpiece 12, as noted above, may be formed from only the two portions of the tubular member 104 and the anchoring member 100. As discussed above the mouthpiece 12, may then be connected to a selected vacuum and/or salvia replacement source for treatment of the user.

The anchoring member 100 may include specially selected structure including non-custom, semi-custom, custom or patient-specific shapes, dimensions, or a combination thereof. For example, the foam member 100 may be die cut or molded to have a selected shape. In various embodiments, the anchoring member 100 may have a shape that is generally a "U" and/or a "C" and/or horseshoe shaped to fit naturally in a mouth around the dental arch. The anchoring member 100 may have a height 100*h* of about 5 mm to about 20 mm, including about 11 mm. The anchoring member 100 may have a width 100*w* of about 5 mm to about 10 mm, including about 7.6 mm. The anchoring member 100 may have a length 100*l* of about 10 mm to about 70 mm, including about 50 mm. The anchoring member 100 may have a span of about 5 mm to about 100 mm, including about 20 mm to about 40 mm.

The tubular member 104 may have the opening 112*o* formed such that it may move along a length or portion of the anchoring member 100. As illustrated in FIG. 15B, the tubular member 104 may be moved to the position illustrated in phantom tubular member 104*c*. Thus, even during use, the user or assistant may move the tubular member 104 relative to the anchoring member 100 and/or relative to the user's mouth for various reasons. Moving the tubular member 104 may assist in comfort to the patient.

More than one tubular member 104 may be connected to or positioned on the anchoring member 100. For example, two or more tubes may be connected, such as the tubular member 104 and the tubular member 104*c* (shown in phantom), may be present and connected to the anchoring member 100 simultaneously. In this instance, the tubular member 104 may form suction through the anchoring member 100 and the tubular member 104*c* may provide an oxygen flow to the user. Thus, the mouthpiece may include more than one tube connected to the anchoring member 100.

With reference to FIG. 16 the tubular member 104' may also be used to form the mouthpiece 12 by pushing or moving the foam 100 through the molded loop 220, such as passing the foam 100 through the inner surface 224. The mouthpiece 12 may be formed by efficiently moving the anchoring member 100 through the opening 224 of the anchor or looped portion 220. The foam 100 may be substantially similar or identical to the foam 100 illustrated in FIG. 15A. Further, the tubular member 104' may also be moved by the user or assistant during use of the mouthpiece, as discussed above.

Figure 17:
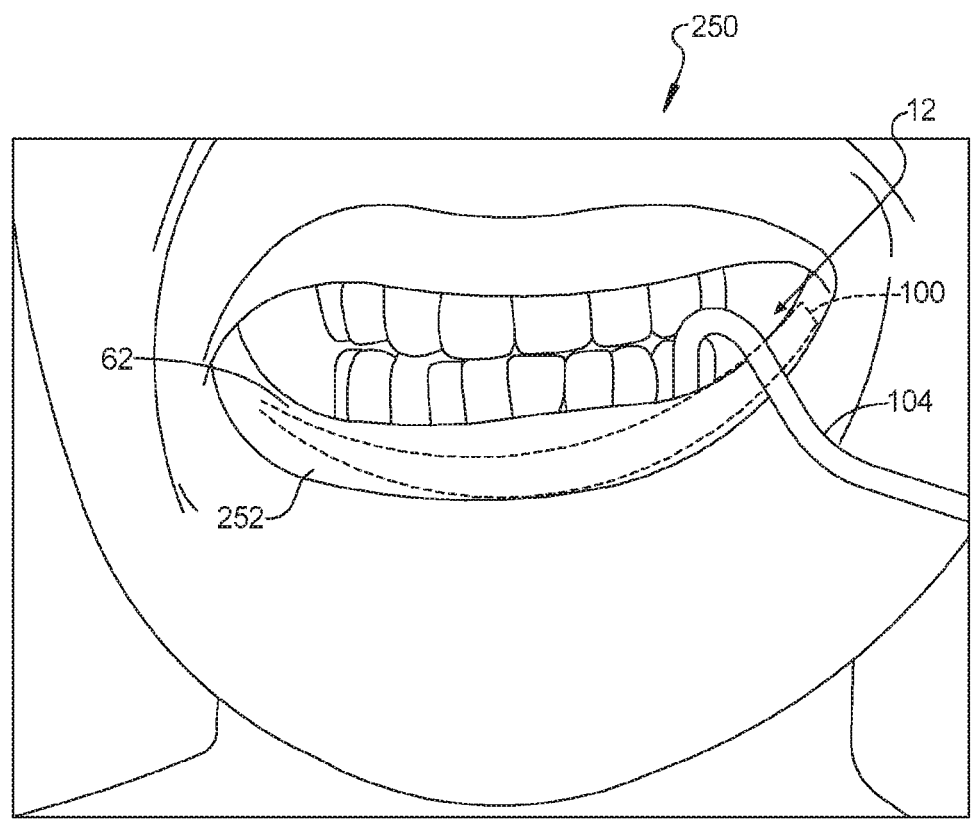
FIG. 17 illustrates embodiments of a mouthpiece positioned in a mouth of the present disclosure.

With reference to FIGS. 15 and 17, the mouthpiece 12 may be positioned relative to a user 250. The mouthpiece 12 may be positioned in the vestibule near the buccal surfaces 62 of the teeth of the user 250. The mouthpiece 12 may be positioned, in various embodiments, so that the tubular member 104 may be looped or hooked over a lip 252 of the user 250. The mouthpiece 12, therefore, may be used to deliver a saliva replacement to the patient 250 and/or remove saliva from the patient 250. The mouthpiece 12 may allow a vacuum to be drawn through the tubular member 104, 104', such as through the cannula of the tubular member 104, 104'. The vacuum is drawn relative to the foam 100 that is positioned relative to the openings 112*o* and 224 of the respective tubular member 104, 104'.

The foam 100 may collect saliva along the length of the foam 100 and it will be drawn through the foam 100 including a substantially open cell configuration and through the respective tubular member 104, 104'. The open cell foam of the foam 100 allows a vacuum to be drawn at substantially only a single location (i.e. the location of the tubular member 104) and a vacuum to drawn liquid throughout the anchoring member 100 into the tubular member 104. Thus, the foam 100 allows a vacuum to be drawn within a large area with the mouth of the user.

Embodiments of anchor member 100 (e.g., foam 100) may not be encapsulated or covered entirely by any other material or member. As discussed herein and illustrated a passage or loop portion of the tubular member 104, 104' may encompass at most or only a portion of the anchoring member 100. The tubular member 104, 104' may cover a selected length of the anchoring member 100, such as generally the outer diameter of the tubular member 104, 104'. The tubular member 104, 104' may cover about 0.5% to about 10%, including about 0.5% to about 3%, and further including about 0.5% to about 1%, of a length from a first terminal end to a second terminal end of the foam 100. Thus, the mouthpiece 12 may be substantially worn by the user 12 as the open cell foam 100 is open to the mouth of the user 250.

In various embodiments, the tubular member 104, 104' may be moved relative to the anchoring member 100 as well and/or in addition to movement relative to the patient. The openings 112*o*, 224 may allow the end of the respective tubes 104, 104' to be moved relative to the anchoring member 100. For example, the opening 112*o*, 224 may be initially positioned at or near a selected end of the anchoring member 100. After a selected period of time, such as 60 minutes, the opening 112*o*, 224 may be moved to a second position such as near a second end of the anchoring member 100. Thus, the tube end opening 112*o*, 224 need not be fixed at a location or position relative to the anchoring member 100.

With reference to FIG. 18, a mouthpiece 412 is illustrated. The mouthpiece 412 may include portions that are similar to those discussed above, including a mouth member or anchoring member 420. The foam or mouth member 420 may be similar to the anchoring member 100, as discussed above. Generally, the anchoring member 420 may be formed of an appropriate shape, such as a U or C shape, to be positioned within the mouth of a user or patient, as illustrated in FIG. 17. Further, the anchoring member 420 may be formed of any material discussed herein.

The anchoring member 420 may be open cell foam that may allow it to be pierced or formed around a nozzle or connection member 430. The nozzle or connection member 430 may be formed to be positioned within the anchoring member 420 such as by pushing, molding, or the like. The connection member 430 includes an external wall 432 that includes or forms an internal passage 434 by an internal surface 484. The connection member 430 may be formed of a selected rigid or substantially rigid material to allow the connection member 430 to be press fit into the foam 420.

The internal passage 434 may pass through the external wall 432 into one or more openings, such as a first opening 440 and a second opening 444. The two openings 440 and 444 may be within the anchoring member 420 (e.g., foam as described herein). Accordingly, a suction or vacuum may be drawn through the opening of passage 434, and also therefore through the openings 440 and 444, relative to the anchoring member 420. When a vacuum is drawn, a vacuum or suction may be formed through the anchoring member 420 through the connection member 430. The connection member 430 may be formed with any appropriate number of openings within the anchoring member 420 and may be fit into the anchoring member 420 in an appropriate manner.

Turning reference to FIG. 19, a connection member 450 may also include an internal passage 454 though an external wall 456 of the connection member 450. The external wall 456 may have one or more ports, through-holes or bores 460 formed therethrough. Accordingly, a suction drawn through the passage or opening 454 may be drawn through the bores 460 such that the anchoring member 420 may have a vacuum drawn therein.

The connection member 450 may further include a barb or reverse angle region 464 that includes a point or projection portion 466 and one or more steps or anchor regions 470. The connection member 450 may be pushed into the anchoring member 420, such as after forming the anchoring member 420. The anchor portion or region 464 the assistant holding the connection member 450 thereto.

In various embodiments, a connection member, such as the connection member 450, may have a portion that extends into the anchoring member 420 a selected distance. The connection member may be pushed into, pierce, and/or be formed into at least a portion of the anchoring member 420. The passages, such as the passages 460, however, are within the anchoring member 420 and may provide a fluid thereto or have a suction drawn therethrough, as discussed above. Thus, the connection member, such as the connection member 450, may extend from more than one side of the anchoring member 420.

With continuing reference to FIG. 18 and FIG. 19, and additional reference to FIG. 19A, a tube or connection portion 480 may connect with the connection member 430 in a selected manner. Near a top or first end 482 of the connection member 430 the opening 434 may be defined by the internal wall 484. The internal wall 484 may include a taper or straight wall portion that engages a taper or connection taper 490 formed at an end 492 of the tube 480. The tube 480 may be similar to the tubular member 104, and it may be connected with source 107. Source 107 may include a pump for drawing fluid by way of a vacuum through the connection member 430 and the anchoring member 420, respectively.

The tapered portion 490 may allow for a sealed connection with the connection member 430. The tapered portion 490 may allow for an easy and efficient connection of the tubular member 480 with the connection member 430 such as by a press fit of the tubular member 480 into the opening 434 ending contact with the internal wall 484. Thus, the tubular member 480 might be connected with the connection member 430 in a removable manner. However, during extended or selected periods of use, the tapered portion 490 is maintained connected with the connection member 430. Additional or alternative materials such as adhesives or sealants may be added to assist in creating or maintaining a seal and/or maintaining a connection of the tube 480 with the connection member 430. Adhesives or sealants may be used as an alternative to the tapered portion 490 as well.

In various embodiments, with reference to FIG. 19 and FIG. 19A, tubular member 104 may be configured as tubular member or tube 510. Tubular member 510 may be formed or have a portion, such as near a distal end 512 that is substantially elastic or elastically deformable. The connection member 450 may include a barb or connection portion, such as an upper rim 522 over that the elastic portion 512 may be expanded and then elastically connects thereto. According, the tube 510 may be elastically deformed over the connection or rib portion 522 and then held thereto, such as with a friction fit or elastic connection during use of the anchoring member 420 as the mouthpiece, similar to that as discussed above. Accordingly, the tube 510 may be selectively connected to the connection member 450 during use or for use of the anchoring member 420 in a suction and/or fluid may be supplied through the tubular member 510 to the connection member 450.

Tubular member 104 may also include a tubular member or tube 510' may also or alternatively include a thread 514. The thread 514 may be an internal thread that is configured to engage an external thread 516 of the connection member 450. The threads 54, 516 may be reversed such that the thread 514 of the tube is external and the thread 516 of the connection member is internal. Nevertheless, the tube 510' may be threadably connected to the connection member 450.

With reference to FIGS. 18-19A, embodiments of tubular members may be selectively connected to the connection members in an appropriate manner, as discussed above. Further, various features or elements may be selectively positioned, such as the elastic portion 512 interconnecting with the connection member 430 rather than the tapered portion. Elements herein may be interchangeable with each other, unless specifically indicated to the contrary.

The mouthpiece of the present disclosure may be provided and used for appropriate applications in selected users, such as human patients. Thus, a gas, such as air or oxygen gas, may be passed to and through the mouthpiece to the user. Also, the mouthpiece may be used with a pump system that may be used to both deliver a fluid and draw a vacuum with the same unit and as selected. Further, a selected agent, such as a sour tasting agent, may be delivered periodically through the mouthpiece to the patient to enhance to help with the production of saliva. Thus, even with a vacuum, the patient may not experience an overly dry mouth and saliva production may be enhanced.

The tubular member of the mouthpiece may be appropriately sized to operate with the anchoring member, such as the anchoring member 100. The tubular member 104 may have the end or opening 112o that is sized to allow or form a suction or vacuum in the anchoring member 100 when a suction is present in the tubular member 104. Thus, the foam may have an exterior dimension that is the same or larger than the opening 112o and/or the anchoring member 100 may be in contact with the interior 224 of the tubular member 104'. The anchoring member 100 may also be smaller than the openings and/or not be in total contact with the internal surfaces if a suction is formed in the anchoring member 100 and/or fluid is sufficiently provided thereto.

Figure 20:
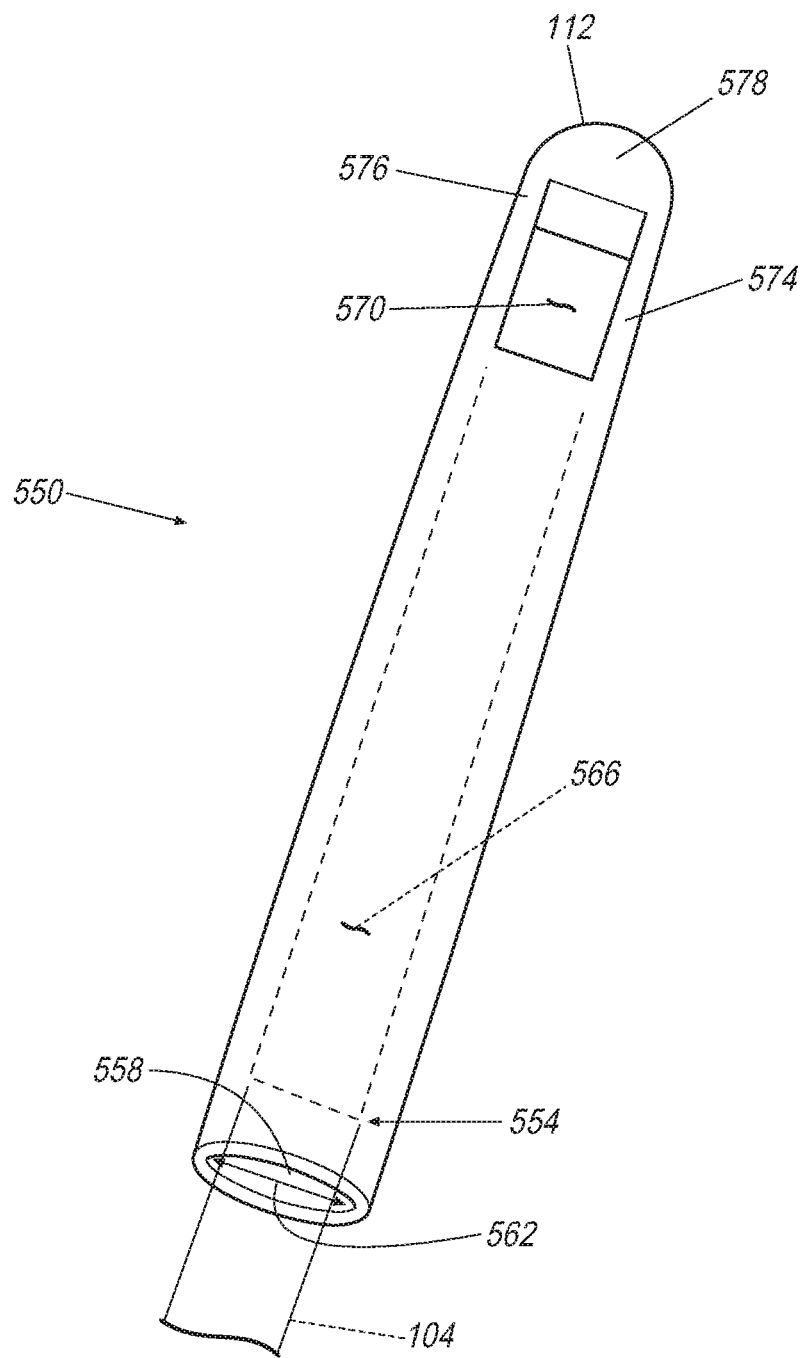
FIG. 20 is a perspective view of embodiments of a connector member of the present disclosure, e.g., integral or connected to a tubular member.
Figure 23:
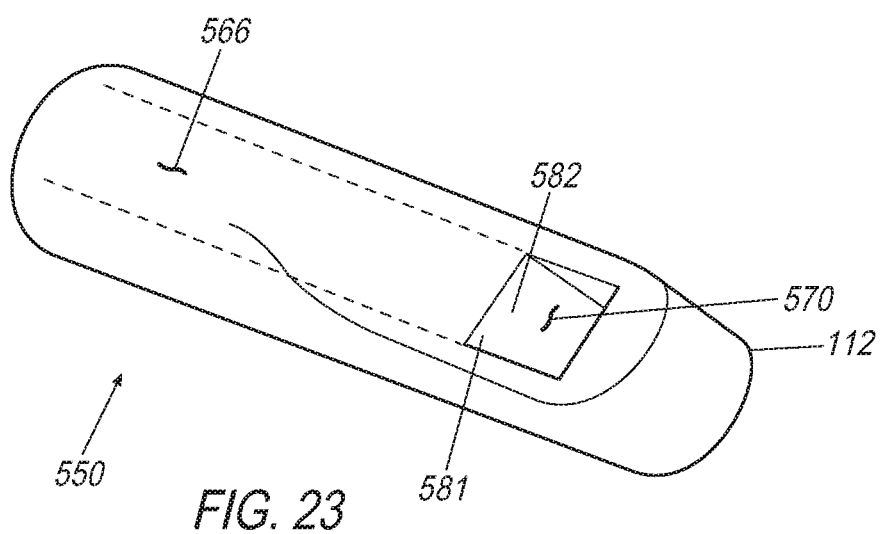
FIG. 23 is a end perspective view of embodiments of a connector member.
Figure 24:
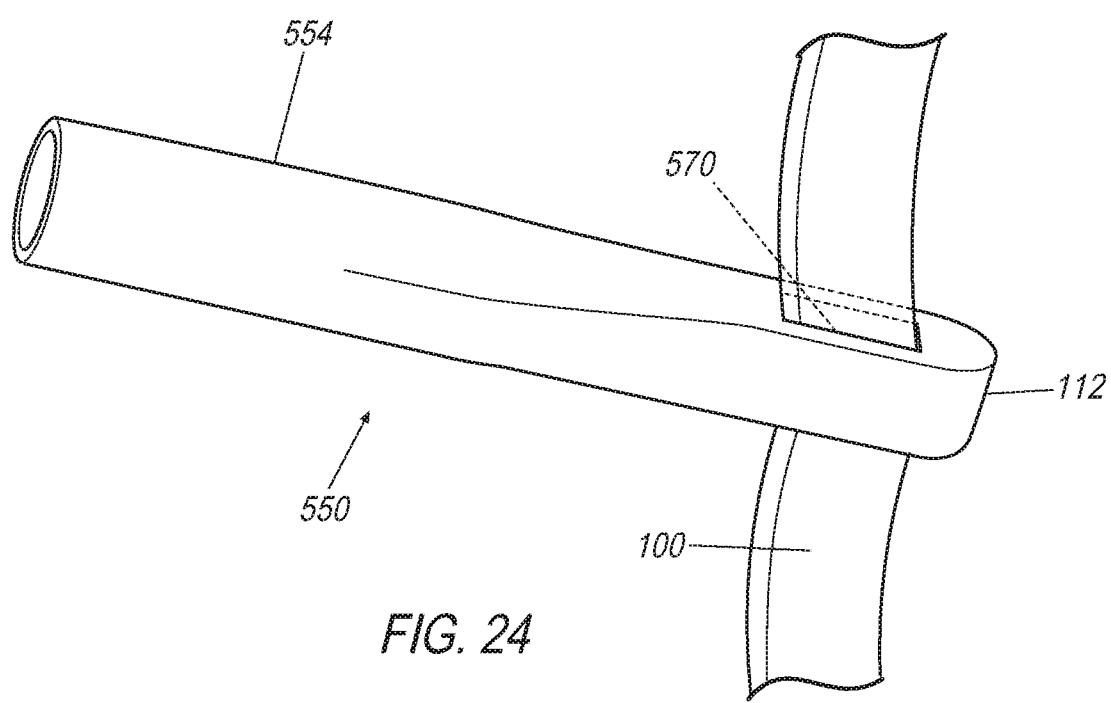
FIG. 24 is a side perspective view of embodiments of a connector member.

Turning to FIGS. 20-26, the mouthpiece 12 may be provided in various embodiments, and may be connected to the tubular member 104 in various manners. With reference to FIG. 20 and FIG. 24, tubular member 104 may include connector 550 or be configured to be received in connector 550. The anchoring member 100 may be received or positioned within connector 550 as an integral part of tubular member 104 or that may be connected to the tubular member 104. For example, the connector 550 may include an exterior wall 554 and an internal surface 558. The internal surface 558 may include an internal cavity, cannula or bore 566 into that the tubular member 104 is positioned. In various embodiments, the internal surface 558 may include a diameter or dimension 562. The dimension 562 may include an internal diameter that is substantially equivalent to or forms a compression or fiction fit with an exterior diameter of the tubular member 104. The tubular member 104 may include any appropriate external dimension that may be engaged within the internal cavity, passage or bore 566, such as against or in contact with the internal wall 558. Further, the connector 550 may be fixed to the tubular member 104 in one or more selected manners, such as with a bonding or adhering material (e.g. glue), a mechanical crimping or compression, or other appropriate connections.

The tubular member 104, therefore, may be held relative to the connector 550 for various purposes. For example, as illustrated in FIG. 20, the tubular member 104 is positioned within the connector 550. The connector 550, including the internal passage 566, allows a vacuum to be drawn through the connector 550 and/or material to be provided through the connector 550 from an end of the connector 550. The end of the connector 550 may include a passage 570 to which or from which a material is delivered or withdrawn.

Figure 21:
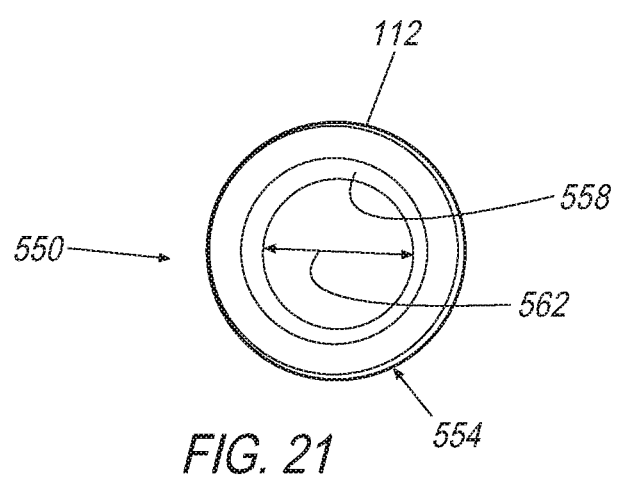
FIG. 21 is an end view of embodiments of a connector member.
Figure 22:
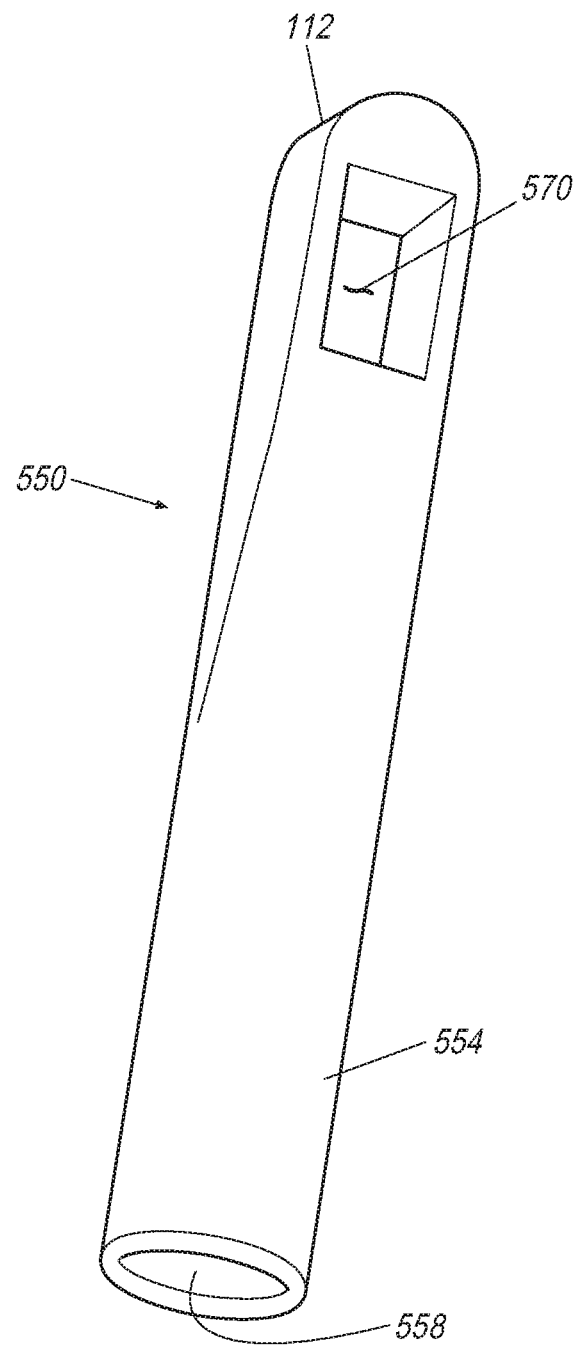
FIG. 22 is a perspective view of embodiments of a connector member.

With reference to FIG. 20 and FIG. 21, and further reference to FIG. 23, the connector 550 may include a capture region including a first side wall 574, and a second side wall 576. Further a terminal end wall 578 may also be provided to enclose the passage 570. The internal cavity, bore or passage 566 may include an opening or end bore 582 at or near the passage 570. Accordingly the internal passage 566 may extend through the connector 550 into the passage or capture portion 570 via the open end 582. The opening 582 allows a suction that is drawn through the tubular member 104 to be drawn through the connector 550 and from the passage 570. Further, as discussed above, material may be provided through the connector 550 to the passage 570, in various embodiments.

As shown in FIG. 24, a selected material such as hydrophilic foam of the anchoring member 100 may be positioned through the passage 570. The foam anchor or mouthpiece foam 100 may be positioned through the passage 570. In various embodiments, the anchoring member 100 may include an external dimension that forms an interference fit with the passage 570, such as engaging the side walls 576 and 574 and/or the terminal wall 578 and the bottom or internal surface 581. Accordingly, the anchoring member 100 may be pushed or pulled through the passage 570. The relative sizes allow the foam 100 to be held relative to the connector 550 for use, such as described herein. The anchoring member 100 may also be otherwise connected to the connector 550, such as with a crimp, adhesive, or the like.

The connector 550 may allow for connection of the tubular member 104 to the mouthpiece 12 or anchoring member 100. In various embodiments, such as those described herein, the suction may be drawn through the tubular member 104 and through the connector 550, such as through the terminal end passage 582. The suction drawn through the terminal end passage 582 may be then drawn through the anchoring member 100 to allow suction to be made at a selected position such as within an oral cavity of a user as discussed above.

Figure 14C:
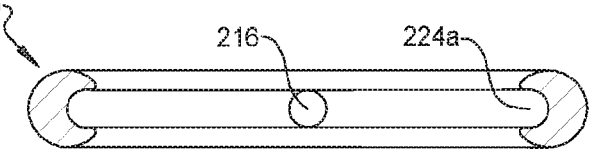
Figure 25:
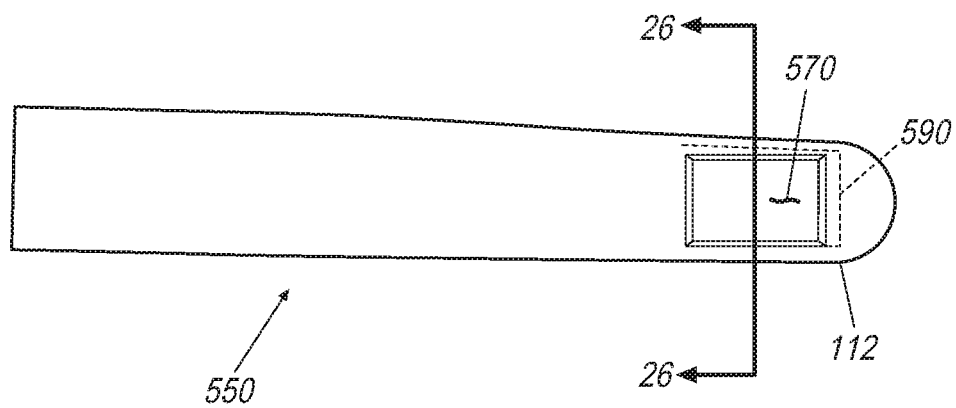
FIG. 25 is a side view of embodiments of a connector member.
Figure 26:
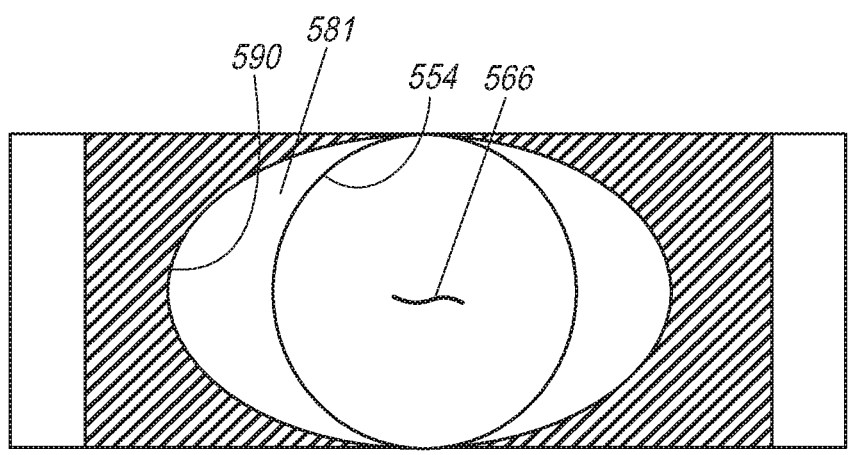
FIG. 26 is a partial cross-sectional view of embodiments of a connector member, e.g., relative to FIG. 25.

In various embodiments, with reference to FIG. 25 and FIG. 26, the terminal end may include a groove or depression 590 at or near the passage 570. Various depressions or grooves, such as internal grooves in the side walls 576, 574 and/or the terminal end 578 may form the groove 590. Accordingly, an internal passage or dimension may be made such as with the internal arch or groove 590 as illustrated in phantom in FIG. 25. The internal groove or arch may be similar to the internal depression or groove 224 of the hoop 220, as illustrated in FIG. 14C, discussed above. The groove 590 may allow for assisting in formation of suction around the anchoring member 100, in various embodiments. Further, the connector 550 may be used for delivery of material to the anchoring member 100 and not only for suction from the anchoring member 100.

The connector 550 may be connected to the tubular member 104 for various purposes, such as discussed above. The tubular member 104 may be connected to source 107 including, for example, a positive, negative or alternating pressure system, a suction or vacuum system, a pump system, a fluid delivery system, or other appropriate system to withdraw and/or provide a material to the anchoring member 100 or other appropriate member.

In various embodiments, the connector 550 may be formed to include selected properties. For example, the connector 550 may be formed of a material to include a property that is substantially non-damaging to teeth of a user. The connector 550 may, therefore, include a selected flexibility or softness. The connector may include selected properties (e.g. stiffness or rigidity) for maintaining an opening there through and/or adhesion or fixation to the tubular member 104. In various embodiments, the connector 550 may be formed of a material with a flexibility to maintain the opening, but has appropriate adhesion properties to the tubular member 104. Appropriate materials may include tubing such as tygon 100-65 tubing including or having medical grade and human contact features. Accordingly, the connector 550 may be used in a selected position, such as within an oral cavity of a user, for purposes such as those described herein. The connector 550 may be connected to the anchoring member 100 (e.g., first anchoring member) in a manner similar to that described herein, such as passing the foam member 100 through the passage 570 of the connector 550 in a manner similar to passing the anchoring member through the loop 220, as discussed above.

Figure 27:
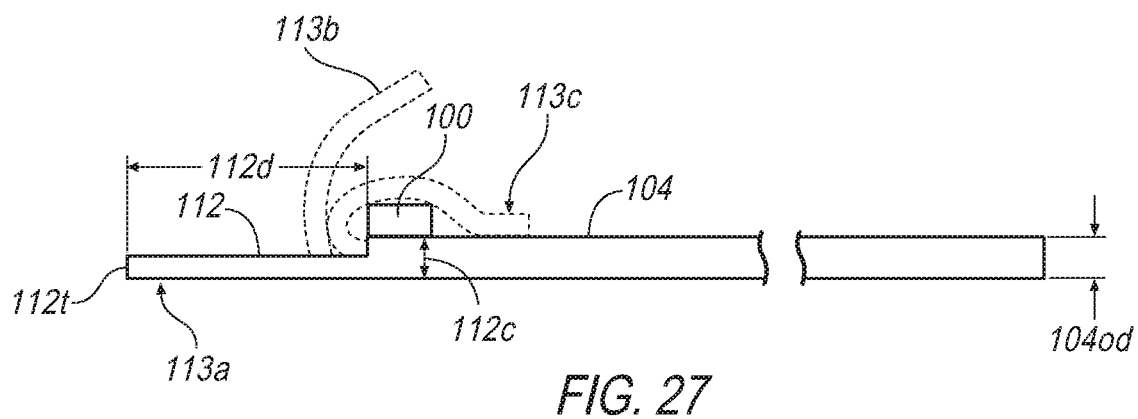
FIG. 27 illustrates a side view of embodiments of an exemplary mouthpiece, e.g., in flattened, partially wrapped and wrapped configurations.
Figure 28:
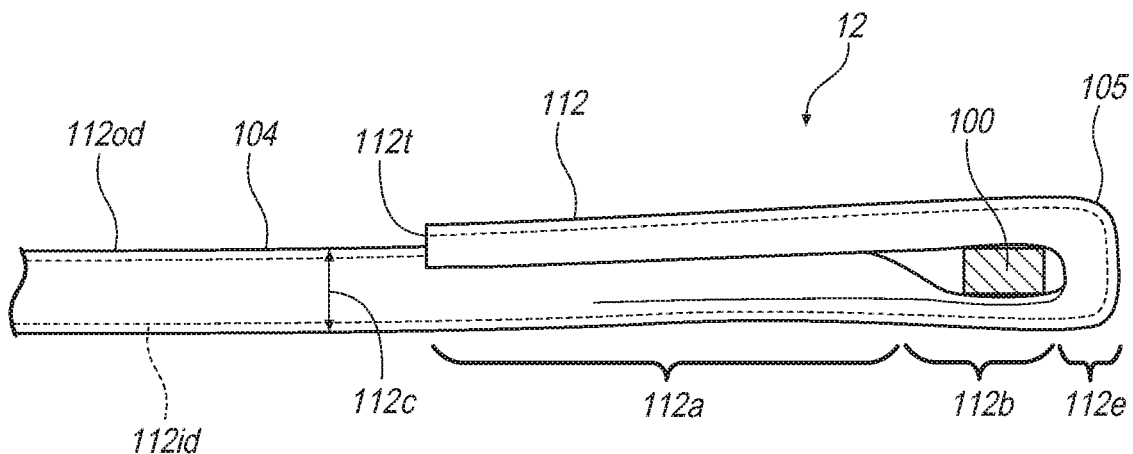
FIG. 28 illustrates a side view of embodiments of an exemplary mouthpiece, e.g., in a wrapped or assembled condition.

FIGS. 27-41 further illustrate mouthpiece 12. As shown in FIG. 27, mouthpiece may include engagement member 112 having a flattened configuration 113a, a partially closed configuration 113b, and an annularly closed configuration 113c. As further shown in FIG. 28, engagement member 112 may be annularly disposed about anchoring member 100. Engagement member 112 may plastically or elastically formed about anchoring member 100. Engagement member 112 may be formed about anchoring member 100 and/or attached to a body portion of tubular member 104, e.g., by way of a heat bond, adhesive or insert molding.

Figure 29:
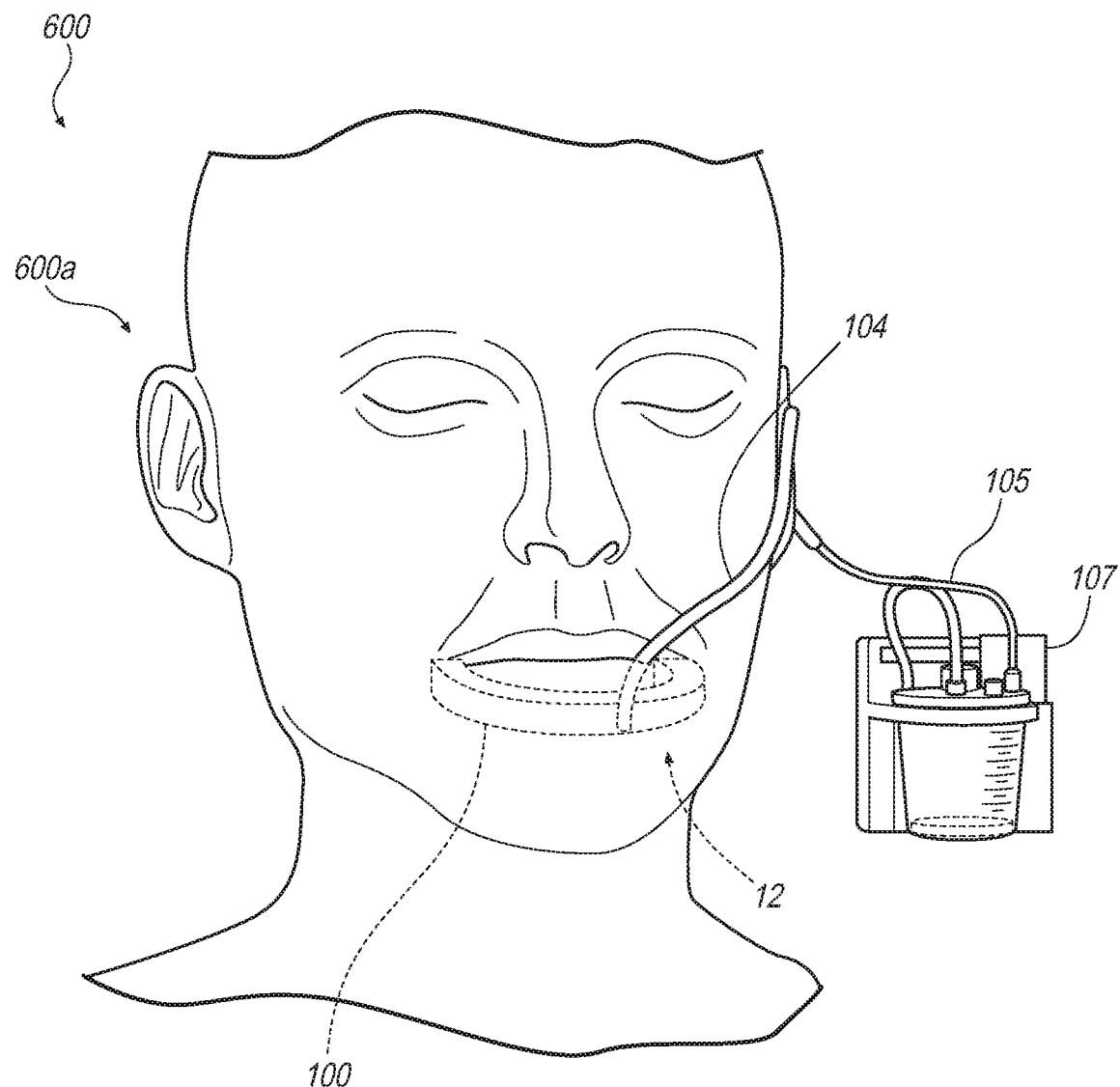
FIG. 29 illustrates a perspective view of embodiments of an exemplary mouthpiece positioned in a user, e.g., a single-anchor or single-flow mouthpiece.
Figure 30:
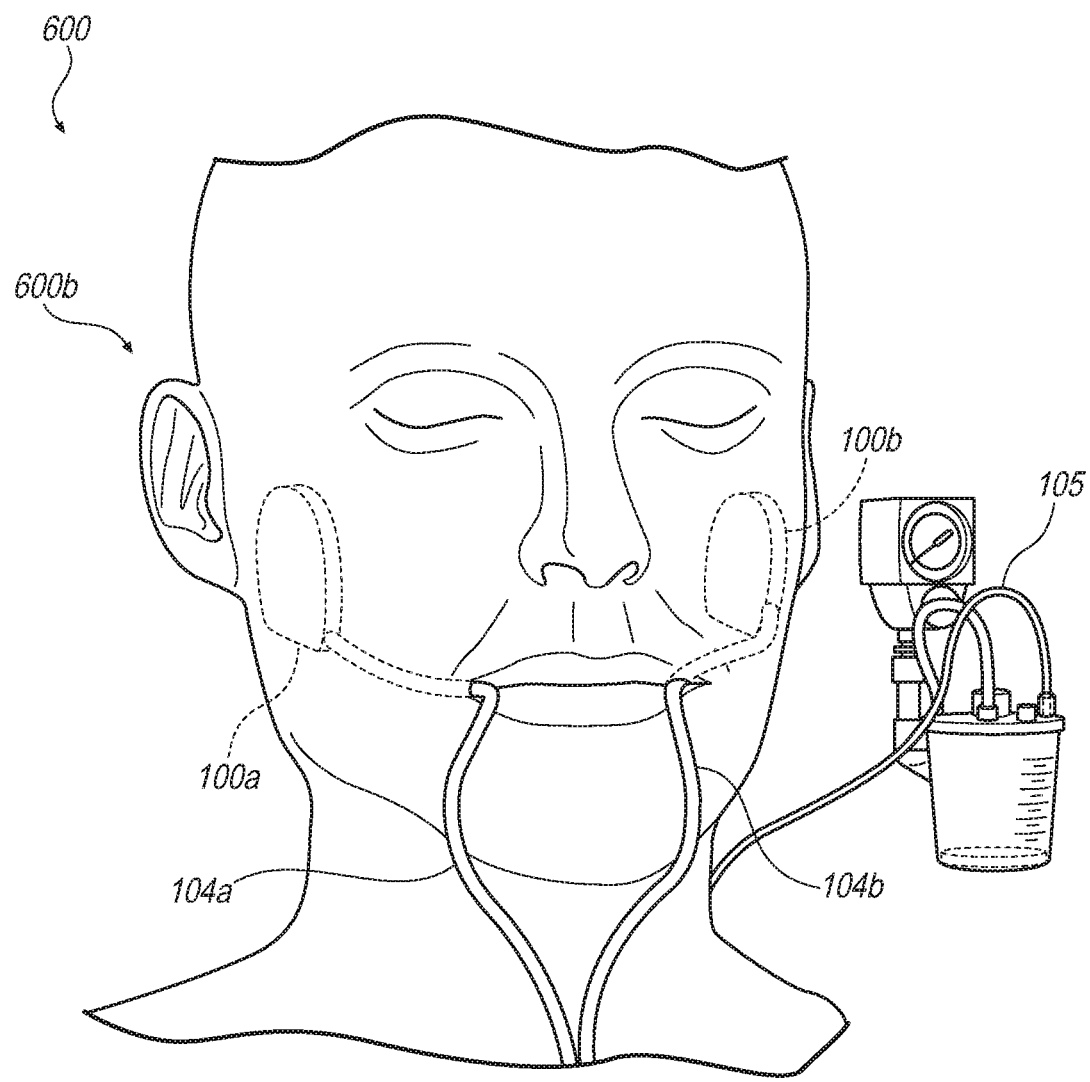
FIG. 30 illustrates a perspective view of embodiments of an exemplary mouthpiece positioned in a user, e.g., a multi-anchor or multi-flow mouthpiece.
Figure 31:
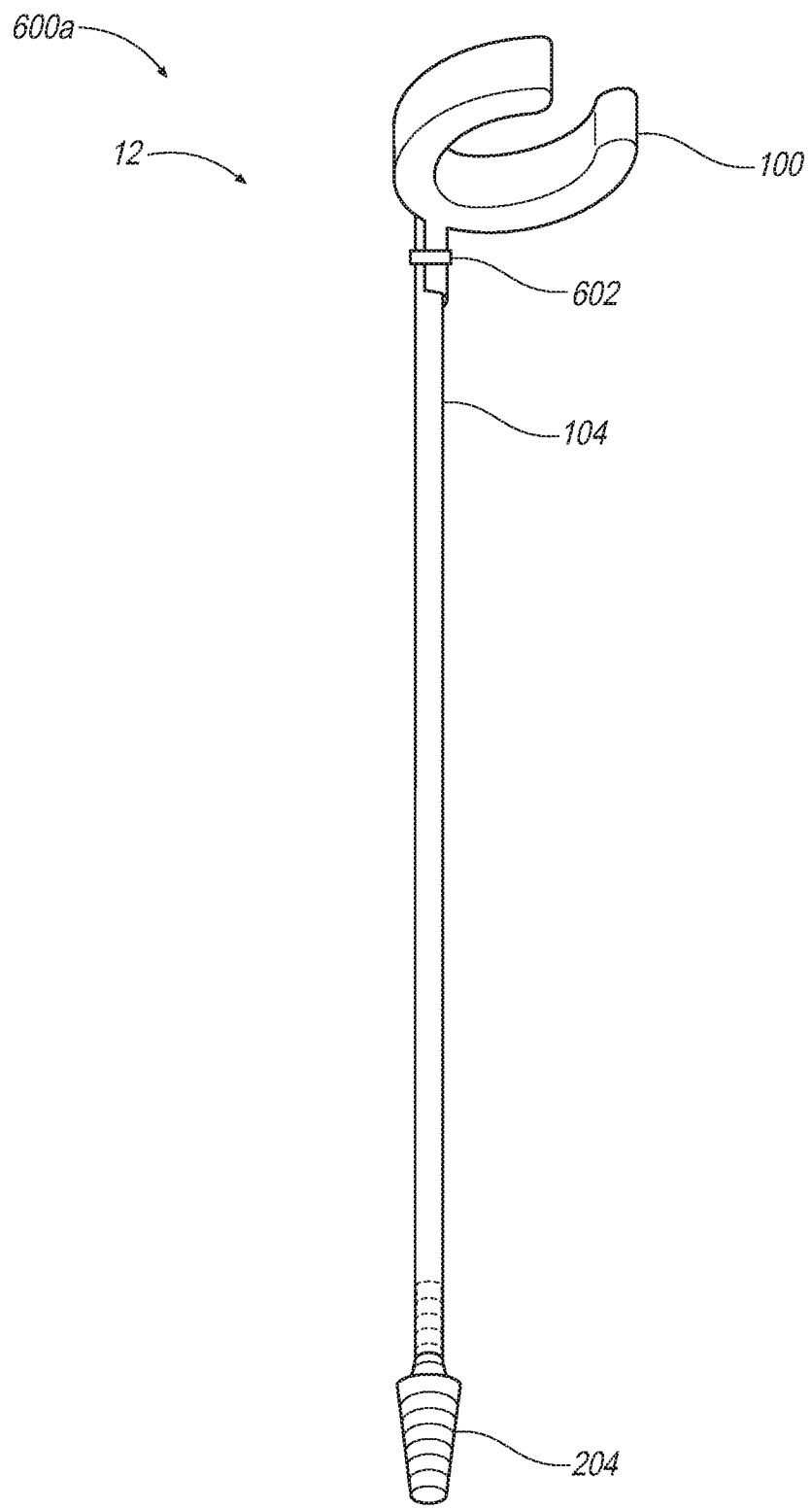
FIG. 31 illustrates a perspective view of embodiments of an exemplary mouthpiece, e.g., as shown in at least FIG. 29.

FIGS. 29-32 illustrate system 600 including mouthpiece 12. As shown in FIGS. 29 and 31, system 600a may include mouthpiece 12 configured as a unitary anchor structure positioned in a body cavity such as a mouth. Mouthpiece 12 may include anchoring member 100 and tubular member 104. Tubular member 104 may be connected to source tubing 105 and source 107. As shown in FIG. 29, anchoring member 100 may be positioned along the gum line of the user, e.g., symmetrically or asymmetrically spanning from the anterior gum line toward the posterior gum line. Anchoring member 100 may symmetrically or asymmetrically span from an incisor area, to a canine area, to a premolar area, and to a molar area of one or both sides of the mouth. Anchoring member 100 may end near any of the canines, premolars, or molars. Anchoring member 100 may be symmetrically or asymmetrically pre-formed, shaped, and/or positioned along the gum line, e.g., extending to the canines or premolars of one side but extending to the premolars or molars of the other side.

As shown in FIG. 31, mouthpiece 112 may include anchoring member 100, tubular member 104, connector 204, and joining member 602. Connector 204 may include first and second ends with barb connections to be received in tubular member 104 and source tubing 105 in communication with source 107 or directly into source 107. Joining members 602 may include any structure or technique to secure anchoring member 100 to tubular member 104, e.g., an elastic, rubber, plastic or metal band, adhesive, heat bond, ultrasonic bond, or press fit. Joining members 602 may be an elastic material or a heat bondable material configured to apply a radially inward, compressive force to secure anchoring member 100 to tubular member 104.

Figure 32:
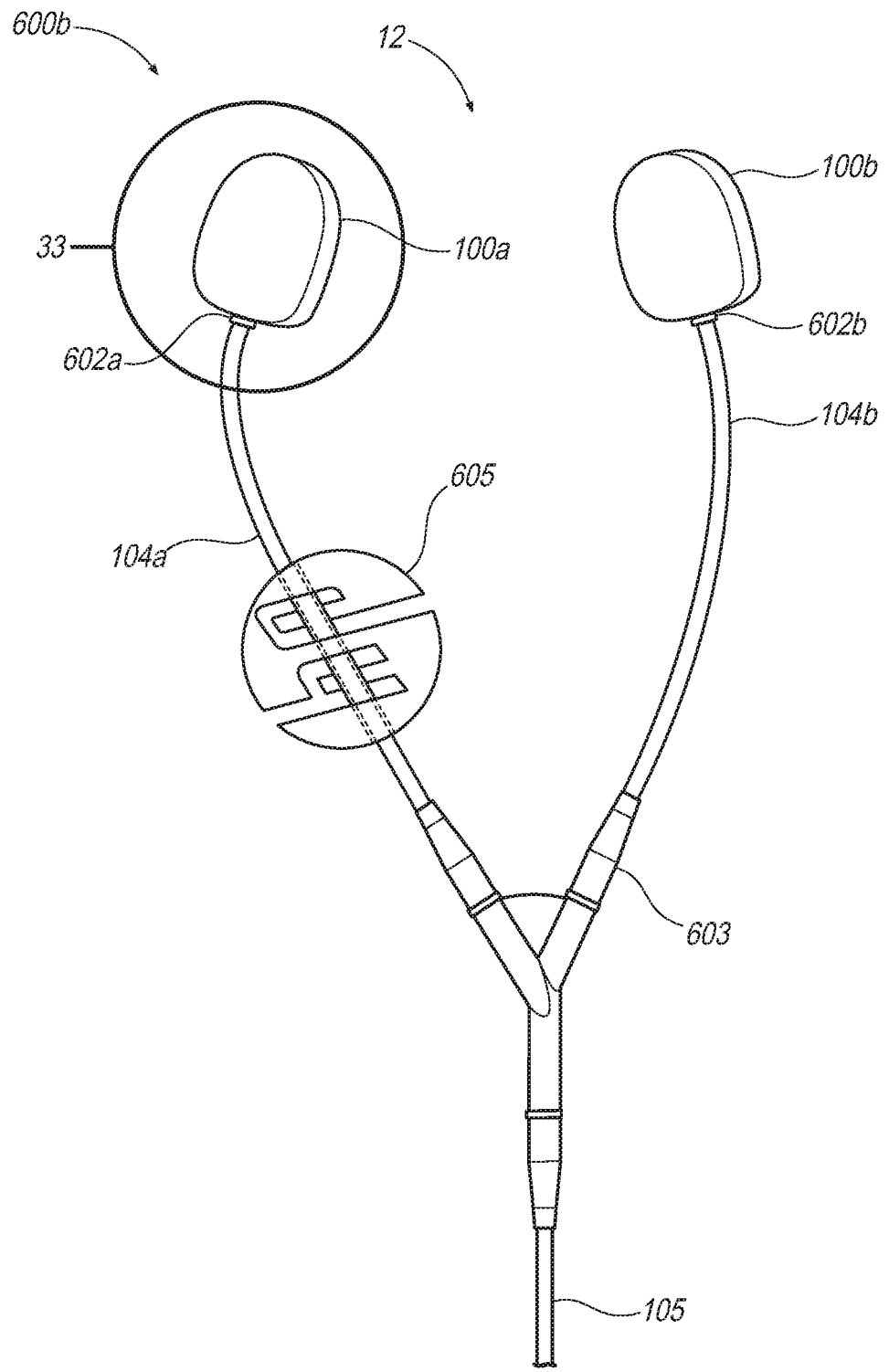
FIG. 32 illustrates a perspective view of embodiments of an exemplary mouthpiece, e.g., as shown in at least FIG. 30.

Referring to FIGS. 30 and 32, system 600b may include mouthpiece 12 may be configured as a multi-anchor structure positioned in a body cavity such as a mouth. This may include first and second anchors members 100a, 100b. First and second anchoring members 100a, 100b may be positioned on opposing sides of the body cavity. First and second anchoring members 100a, 110b may be positioned along the gum line of the mouth, e.g., the opposing posterior areas of the gum line. Anchoring members 100 may symmetrically or asymmetrically span from an incisor area, to a canine area, to a premolar area, and to a molar area of one or both sides of the mouth. Anchoring members 100 may end near any of the canines, premolars, or molars. First and second anchoring members 100a, 100b may be asymmetrically shaped and/or positioned along the gum line, e.g., extending to the canines or premolars of one side but extending to the premolars or molars of the other side. First and second anchoring members 100a, 100b may be positioned along the upper or lower gum line, a combination thereof. First and second anchoring members 100a, 100b may be symmetrically or asymmetrically pre-formed, shaped or positioned relative to each other.

With further reference to FIG. 32, system 600b including mouthpiece 600b including first and second anchoring members 602a, 602b. First and second anchoring members 602a, 602b may be connected to a fluid transfer conduit including a main conduit that splits into corresponding first and second auxiliary conduits 104a,b, e.g., tubular members 104a, 104b. Interconnect 603 may include first and second receptacles to receive tubular members 104a, 104b and a third receptacle to receive source tubing 105. One or both of tubular members 104a, 104b may be secured relative to a user with clip 605, e.g., relative to one or more teeth or lips of the user.

Figure 33:
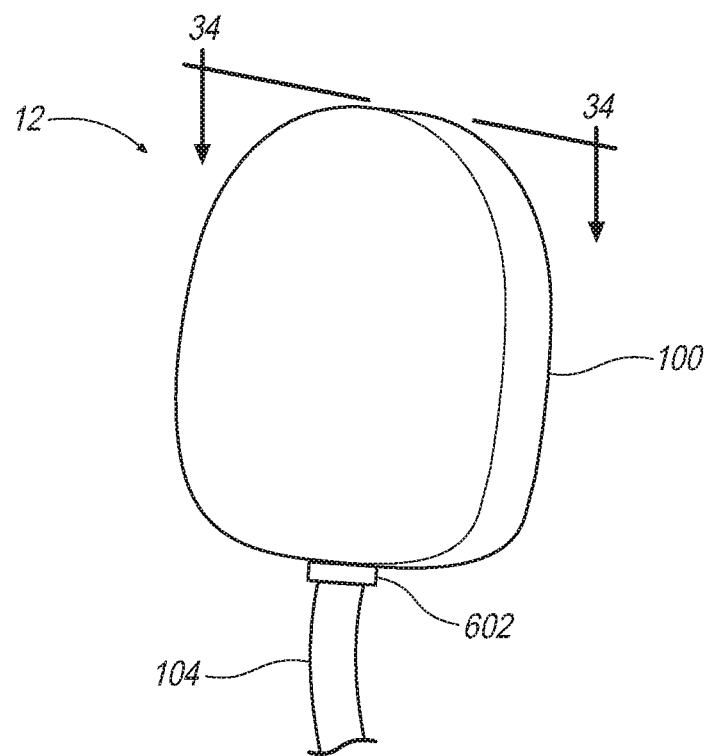
FIG. 33 illustrates a closer view of embodiments of an exemplary mouthpiece including, e.g., an anchoring member of a single-anchor or multi-anchor mouthpiece.
Figure 34:
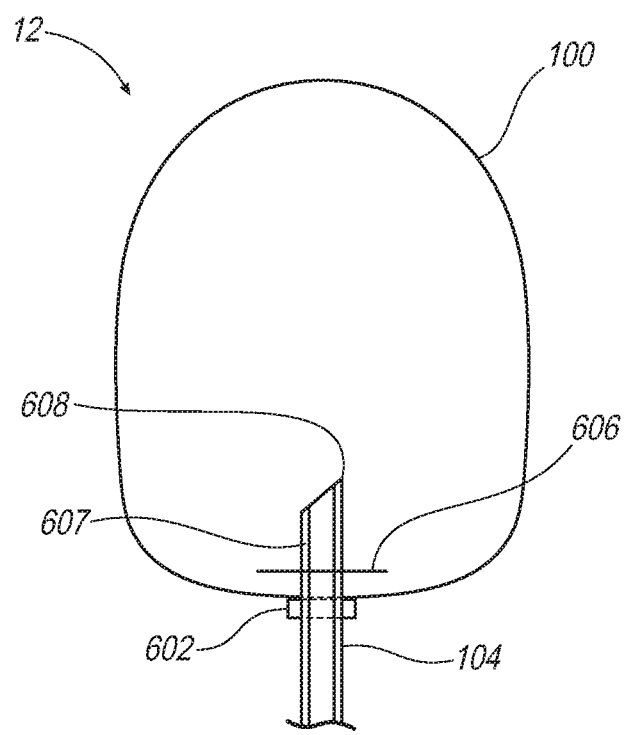
FIG. 34 illustrates a cross section view of embodiments of an exemplary mouthpiece, e.g., as shown in at least FIG. 33.

FIGS. 33-34 illustrate a closer view of mouthpiece 12. Mouthpiece 12 may include anchoring member 100, tubular member 104 and engagement member 602. As shown in FIG. 34, engagement member 602 may include pin 606 that secures anchor 100, tubular member 104, and engagement member 602 together. Engagement member 602 may include tubular extension 607 including leading end 608 that may be tapered. Engagement member 602 may include a sidewall defining a passage therethrough. Engagement member 602, e.g., tubular extension 607, may be configured for the transfer of fluid between anchoring member 100, engagement member 602 and tubular member 104. Engagement member 602, e.g., tubular extension 607, may be slotted, perforated, notched or a combination thereof.

FIGS. 35A, B, C and D illustrate front cross-section, first side cross-section, bottom, and second side cross-section views of mouthpiece 12, and FIGS. 36, 37 and 38 illustrate side, top and bottom views of mouthpiece 12. Anchoring member 100 may include anchor bore 609 configured to receive the tubular extension 607 of engagement member 602. The anchor bore 608 may be configured to permanently or releasably secure engagement member 602 relative to anchoring member 100 while allowing the transfer of fluid therebetween. As shown in FIG. 35D, anchoring member 100 may be configured to receive tubular extension 607 having extension length 610, and may have an anchor length 612.

Figure 39:
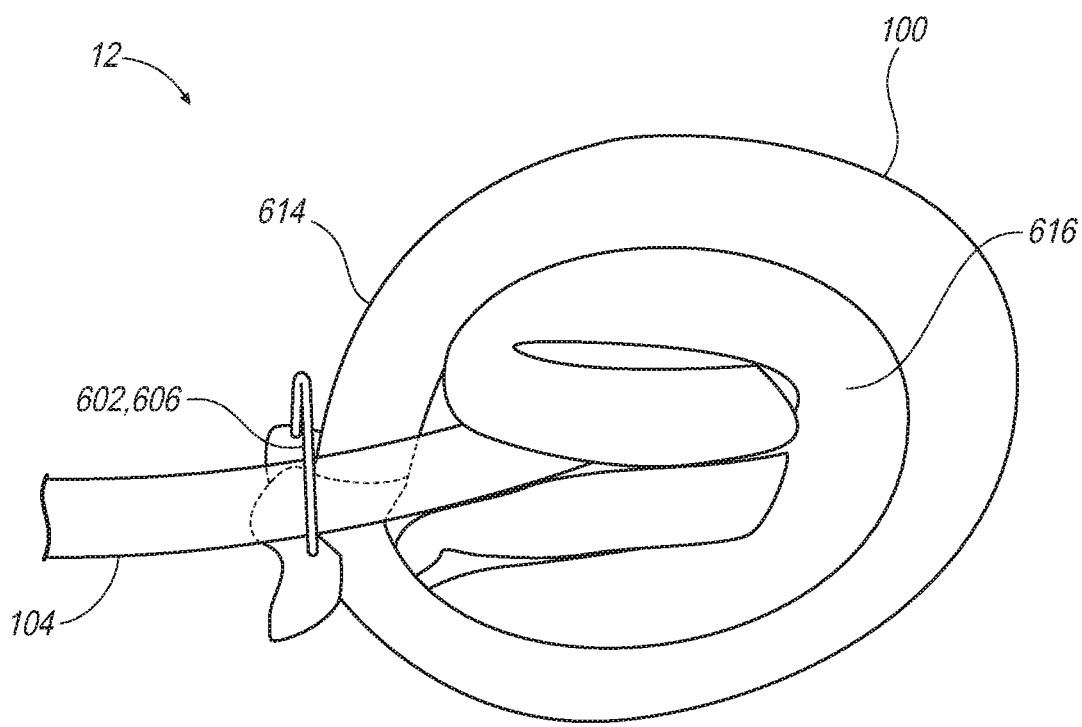
FIG. 39 illustrates embodiments of an exemplary anchoring member including, e.g., a multi-component or multi-layered anchor.
Figure 40:
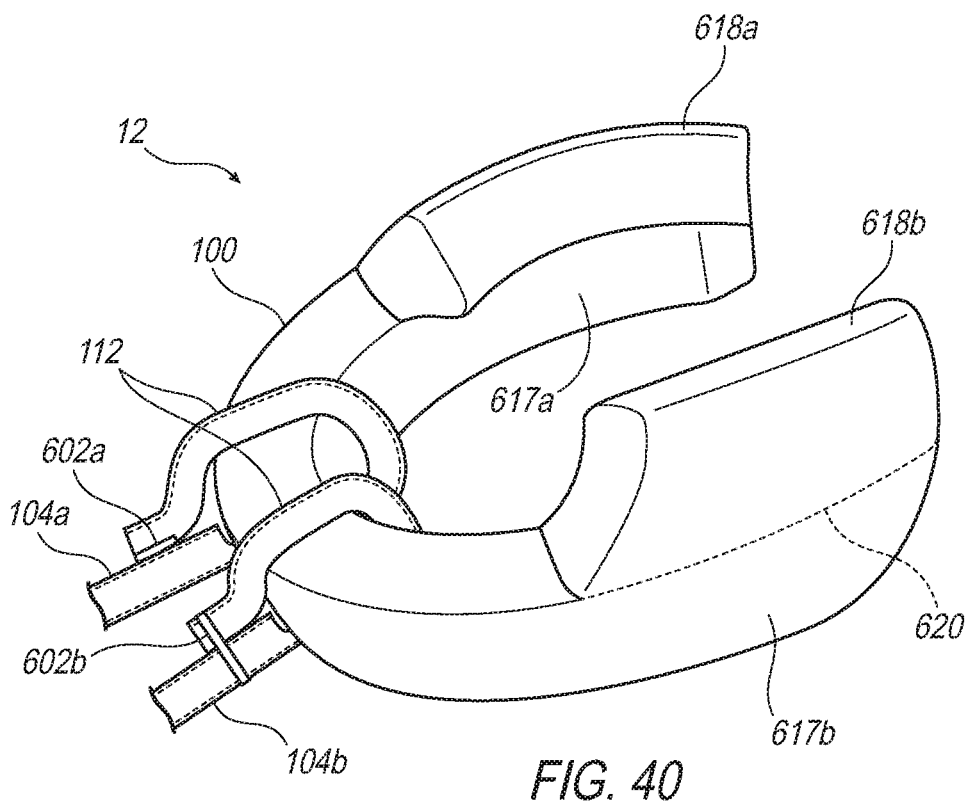
FIG. 40 illustrates embodiments of an exemplary mouthpiece including, e.g., a multi-component or multi-layer anchoring member with multiple extensions.
Figure 41:
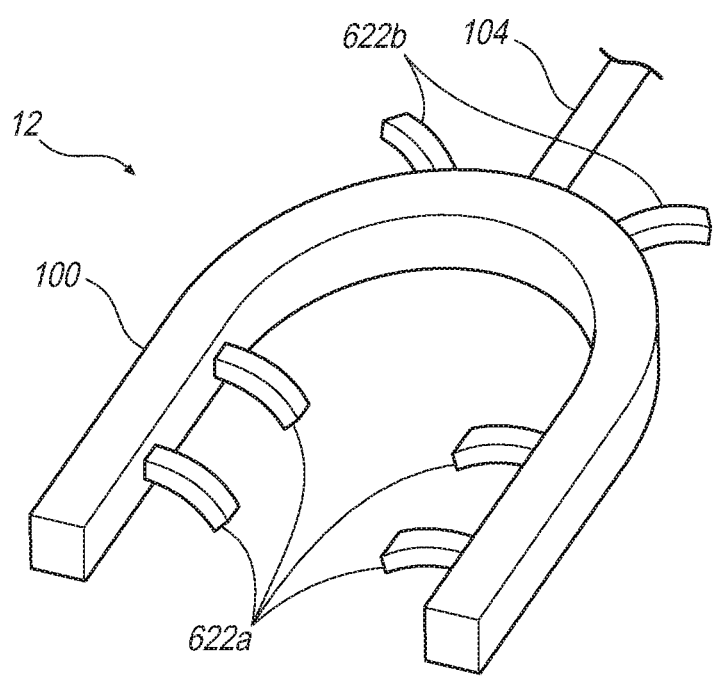
FIG. 41 illustrates embodiments of an exemplary mouthpiece including, for example, an anchoring member with teeth clamps.

FIGS. 39, 40 and 41 illustrate exemplary mouthpieces 12. As shown in FIG. 39, mouthpiece 12 may include a multi-component or multi-layered anchoring member 100 including, for example, first or outer layer 614 and second or inner layer 616. Tubular member 104 and anchoring member 100 may be secured to each other by way of joining members 602, pin 606 or a combination thereof.

As shown in FIG. 40, mouthpiece 12 may include one or more tubular members 104a,b with respective annular portions 112, e.g., configured to rotate about anchoring member 100, move or slide along anchoring member 100, and/or apply positive, negative or alternating pressure about a transverse perimeter of anchoring member 100. The annular portion 112 of tubular members 104a,b may be respectively positioned around anchoring member 100 and secured to corresponding proximal portions of tubular members 104a, b, e.g., by way of joining members 602a,b of the same or different types. For example, joining member 602a may include an adhesive or bond, joining member 602b may include a band such as those described herein, or any combination thereof. Tubular member 104a may apply positive pressure, negative pressure or alternating pressure while tubular member 104b applies the same pressure, the other of the negative or positive pressure, or alternatingly apply the same, different or opposite pressure as tubular member 104a.

Mouthpiece 12 may include with one or more extrusions or layers. Mouthpiece 12 may further include first and second lower or base portions 617a,b and first and second upper or extension portions 618a,b, e.g., configured to upwardly extend, curve over, and/or be positioned on a premolar and/or molar area. The first and second lower or base portions 617a, 617b and first and second upper or extension portions 618a,b may be manufactured as an integral or unitary component or separate components that are connected along separation line 620.

As shown in FIG. 41, anchoring member 100 may include clamps 622 made of a metal, plastic or elastic material and configured to secure anchoring member 100 relative to teeth or lips, e.g., by extending inwardly and downwardly, outwardly and upwardly, or any combination thereof. Anchoring member 100 may include clamps 622a extending inward from first and second sides and/or the front of anchoring member 100 and/or clamps 622b extending outward from the front and/or the first and second sides of anchoring member 100, e.g., to engage teeth with clamps 622a and/or be positioned around a lip with clamps 622b.

Figure 42:
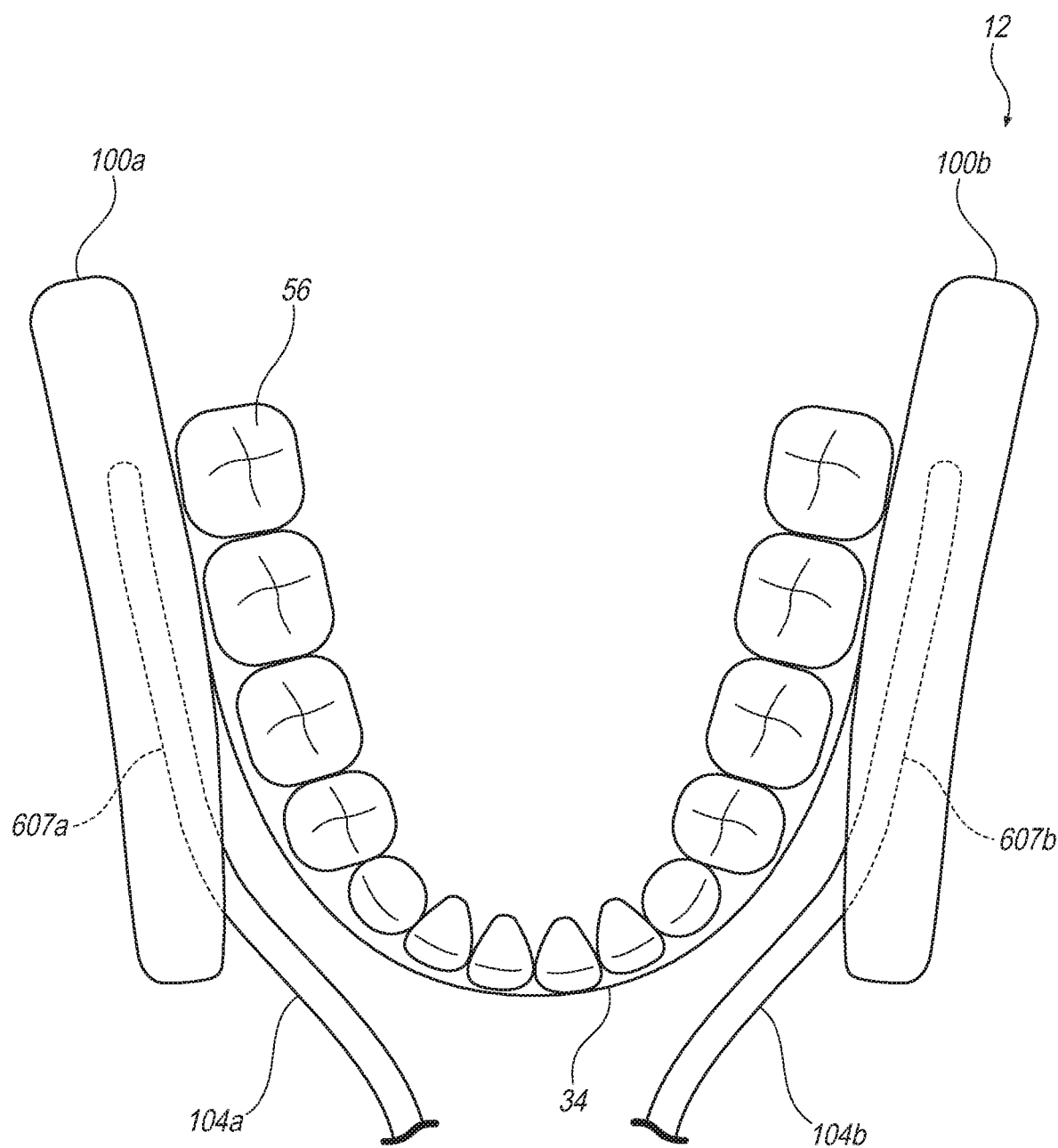
FIG. 42 illustrates embodiments of an exemplary mouthpiece, for example, positioned relative to a body cavity such as a mouth.
Figure 43:
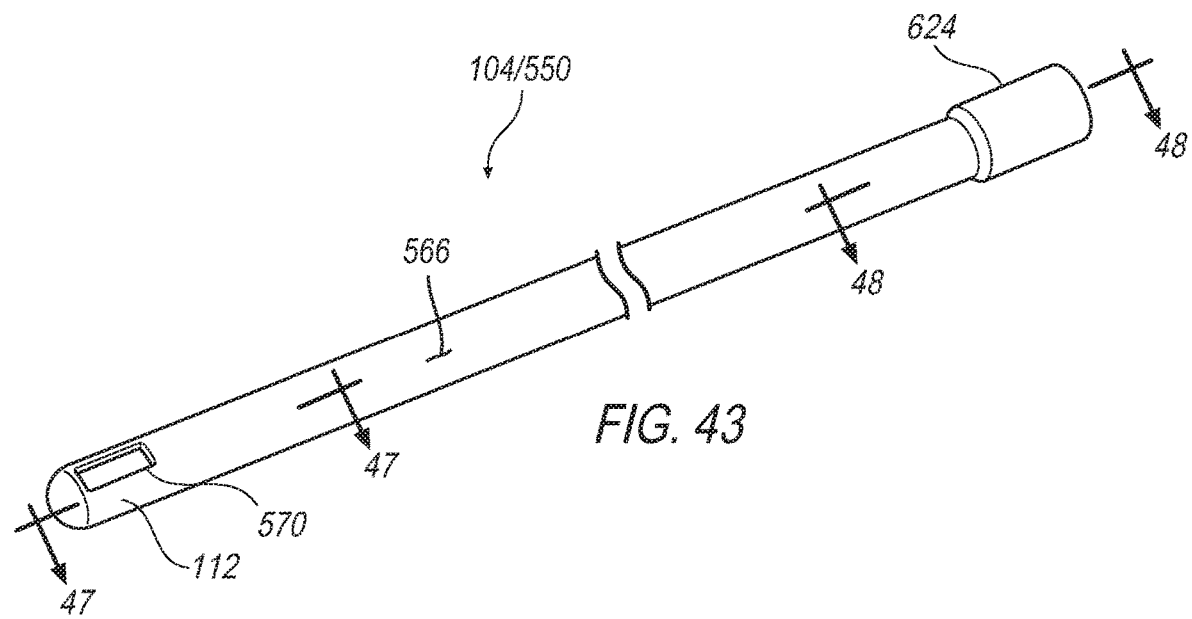
FIG. 43 illustrates embodiments of a perspective view of an exemplary connector member of the present disclosure.

FIG. 42 illustrates mouthpiece 12 positioned relative to a mouth of a patient. Mouthpiece 12 may include anchoring members 100a,b positioned on opposing sides of vestibule 34. Tubes 104a,b may be positioned through respective first and second inner sidewalls of anchoring members 100a,b. Alternatively, tubes 104a,b may be positioned through respective first and second leading ends or first and second outer sidewalls of anchoring members 100a,b. Anchoring members 100a,b may include anchor bore 609 configured to receive the tubular extension 607.

Figure 44:
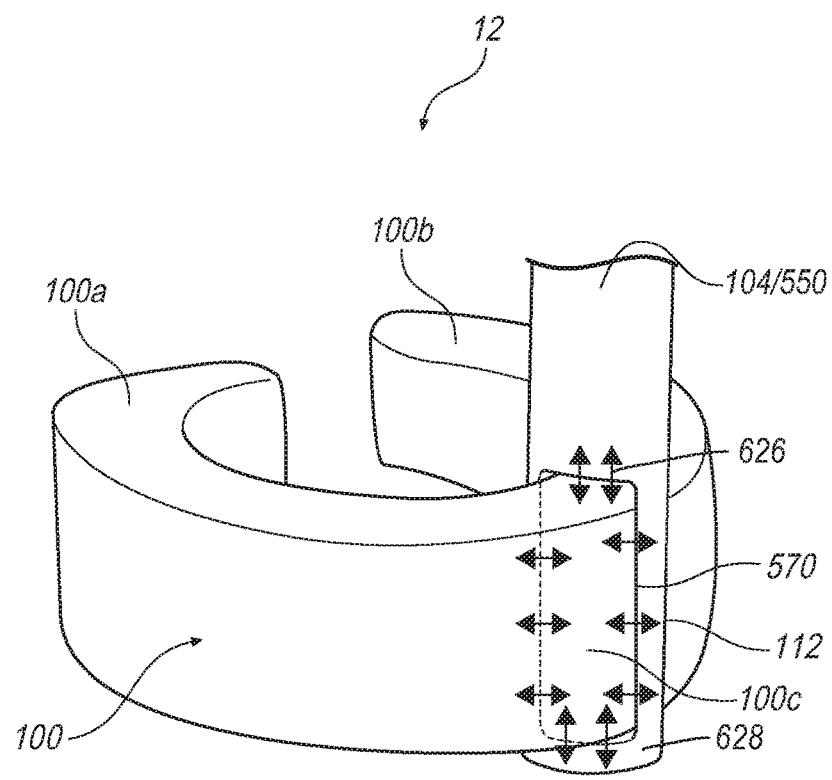
FIG. 44 illustrates embodiments of a perspective view of an exemplary mouth piece including, for example, an anchor member positioned in a connector member.
Figure 45:
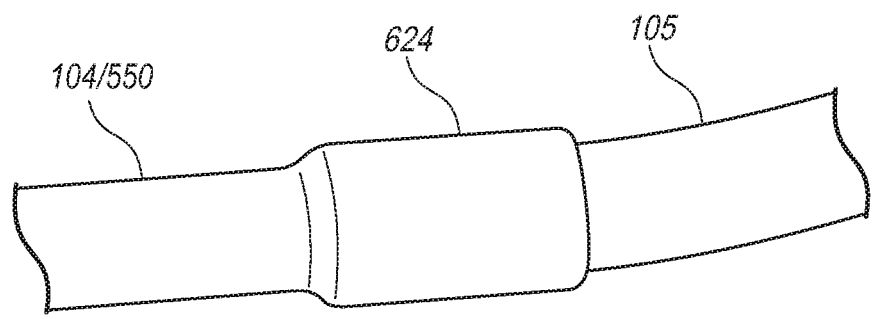
FIG. 45 illustrates embodiments of a perspective view of a fluid transfer portion connected to a source tubing.
Figure 46:
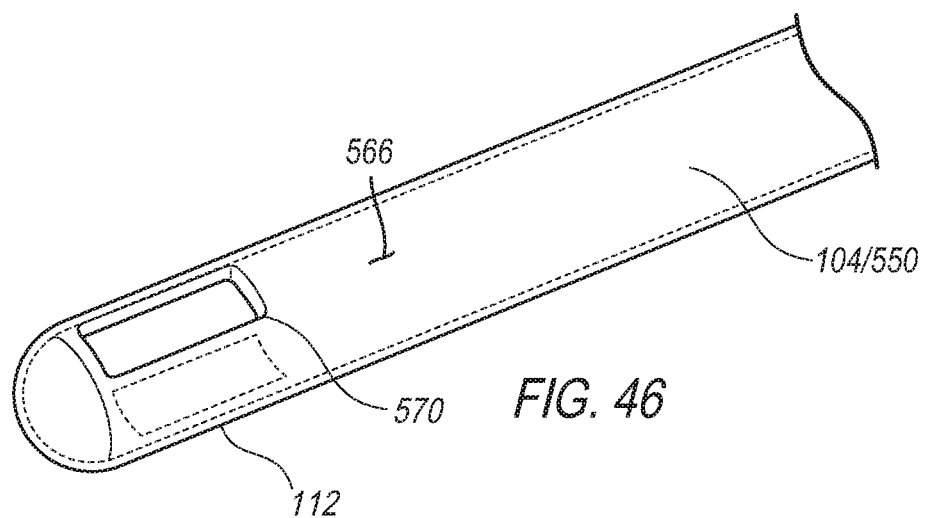
FIG. 46 illustrates a closer perspective view of embodiments of a capture portion.
Figure 47:
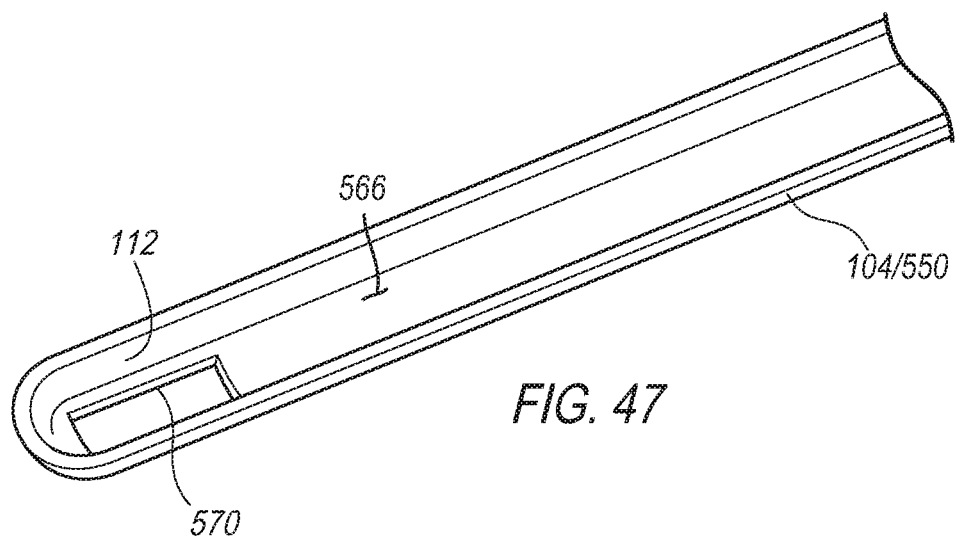
FIG. 47 illustrates a perspective cross-section view of embodiments of a capture portion.
Figure 48:
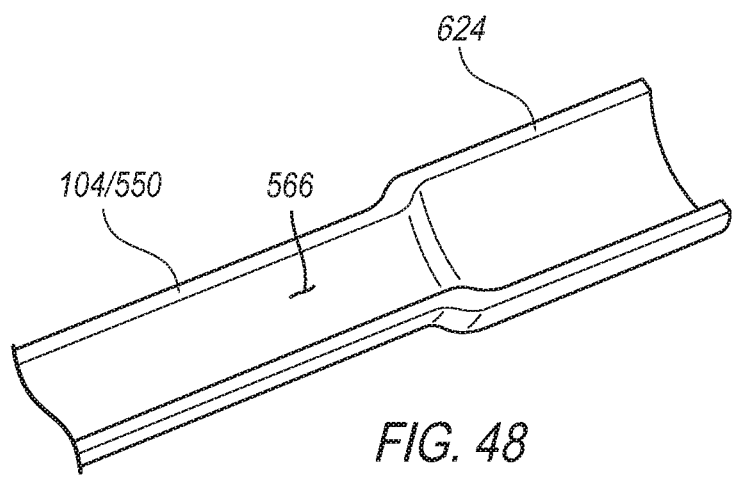
FIG. 48 illustrates a perspective cross-section view of embodiments of a fluid transfer portion.

With reference to FIGS. 43-48, embodiments of mouthpiece 12 may include tubular portion 104 including or received in connector 550 as described above. Tubular portion 104 or connector 550 may include cavity 566. As shown in FIGS. 44 and 47, tubular portion 104 or connector 550 may include capture portion 112 with passage 570 transverse to a longitudinal axis of tubular portion 104 or connector 550. Passage 570 may be configured to receive anchoring member 100, e.g., foam member 100. Anchoring member 100 may include a first side 100a, a second side 100b and an intermediate portion 100c, any of which may be positioned in or through capture portion 112. As shown in FIGS. 45 and 48, connector 550 may include fluid transfer portion 624 (e.g., a tubular and/or enlarged portion) configured to receive source tubing 105. Capture portion 112 may be configured to allow anchoring member 100 to slide through passage 570, e.g., along a longitudinal axis of foam member 100. Anchoring member 100 may slide relative to capture portion 112 to reduce irritation to surrounding tissue of the bodily cavity.

As shown in FIGS. 24 and 44, passage 570 may be configured as a capture portion 570 adapted to seal and/or press against anchoring member 100. With further reference to FIG. 44, capture portion 570 may be configured to provide a positive, negative and/or alternating pressure for one-way or multi-direction flow 626, e.g., of fluid to and around a capture portion 570. Flow 626 may be applied to a portion of a transverse area or perimeter of anchoring member 100 (e.g., 1-359 degrees) or an entirety of a transverse area or perimeter of anchoring member 100 (e.g., 360 degrees). Capture portion 570 may include a uniform or varying cavity 628 around anchor member 100, e.g., to optimize the volume and/or direction of flow 626. Capture portion 570 may be configured to allow anchoring member 100 to be selectively positioned or slide relative to anchoring member 100. Connector 550 and/or capture portion 570 may be configured to reduce damage or irritation to surrounding portions of the bodily cavity. Any of the components herein may be secured relative to each other, e.g., capture portion 570 to anchoring member 100, using a pressure bond (e.g., press or friction fit), a chemical bond (e.g., adhesive or glue), ablative bond (e.g., heat bond), energy bond (e.g., ultrasonic energy), or a combination thereof.

Systems and methods may be configured to transfer fluid with respect to a body cavity. The body cavity may include a mouth cavity having a dental arch, a vestibule, and a gum line. The dental arch may have a biting surface. The vestibule is on an outer side of the dental arch. The gum line is on an inner side of the dental arch.

A mouthpiece 12 may have a hydrophilic foam member 100 and a tubular member 104. The tubular member 104 may include an elongated portion and an annular portion 112. The hydrophilic foam member may include first and second lateral extensions being configured to be positioned along the outer side of the dental arch. The annular portion 112 of the tubular member 104 may be configured to be annularly disposed around a transverse perimeter of the hydrophilic foam member while the elongated portion of the tubular member 104 defines a first fluid passage configured to be fluidically coupled to only the transverse perimeter of the hydrophilic foam member 100. A fluid conduit may be coupled to the first fluid passage in fluid communication with a supply source.

The annular portion 112 may include a notched portion configured to be annularly disposed about the hydrophilic foam member 100 and allow fluid transfer by way of positive or negative pressure (e.g., suction) applied to the hydrophilic foam member 100. The annular portion 112 may include a perforated portion configured to be annularly disposed about the hydrophilic foam member 100 and allow suction to be applied to the hydrophilic foam member 100.

The mouthpiece 12 may include a plurality of anchoring members adapted to engage the dental arch along first and second sides of the mouth. The mouthpiece 12 may include a plurality of anchoring or clamp members 622a,b configured to be disposed between adjacent teeth and/or engage the gum line along first and second sides of the mouth.

The supply source may include a pump and a controller configured to regulate the flow of the saliva through the fluid conduit that is fluidically coupled to the hydrophilic foam member 100. The supply source is configured to provide at least one of a fluid supply and a vacuum to the tubular member 104.

Systems and methods may be configured to manage fluid transfer with respect to first and second bodily regions. A fluid transfer conduit (e.g., tubular portion 104) may include a main conduit that splits into a first auxiliary conduit (e.g., tubular portion 104a) and a second auxiliary conduit (e.g., tubular portion 104b). A first anchoring member (e.g., foam member 100a) may include a first bodily engagement portion (e.g., capture portion, notched portion or annular portion 112a) and a first fluid transfer portion (e.g., fluid transfer conduit or tubular member 104a). The first engagement portion 112a may be configured to conformingly engage the first bodily region, and the first fluid transfer portion 112a being in fluid communication with the first auxiliary conduit 104a. The first bodily region may include a first cheek area of a mouth and the second bodily region includes a second cheek area of the mouth. The first bodily region may include first and second cheek areas of a mouth and a second bodily region includes a gum line of the mouth.

A second anchoring member or foam member 100b may include a second bodily engagement portion 112b (e.g., capture portion, notched portion or annular portion 112b) and a second fluid transfer portion (e.g., fluid transfer conduit or tubular member 104a). The second bodily engagement portion 112 may be configured to conformingly engage the second bodily region. The first fluid transfer portion 104 may be in fluid communication with the second auxiliary conduit.

The first anchoring member configured to attach to the first bodily region and the second anchoring member is configured to attach to the second bodily region. The first bodily region may include a lower dental arch adjacent a first tooth on a first side of a mouth, and the second bodily region includes the lower dental arch adjacent a second tooth on a second side of the mouth.

The first auxiliary conduit or tubular member 104a may configured to extend from with a central mouth cavity proper from the first anchoring member to the second anchoring member along an inner gum line. The first tubular member 104 may include a first end fluidly coupled to the first passage, a second end opposite the first end attached to the second anchoring member, and an aperture extending through a wall of the first tube adjacent a front portion of the mouth cavity proper.

The second auxiliary conduit or tubular member 104b may be configured to extend within a vestibule on the first side of the mouth along an outer gum line. The second tubular member 104b may include a first end fluidly coupled to the first passage and a second end extending outside of the mouth.

The second anchoring member 100b may include a second passage extending between a vestibule on the second side of the mouth and a central mouth cavity. The second end of the first tube may be fluidly coupled to the second passage.

Systems and methods may include a portable supply unit adapted to be carried by a user. the portable supply unit including a first fluid system that is configured to fluidly couple to the fluid transfer conduit to transfer fluid with respect to the mouth via the fluid transfer conduit based on first operational settings, a first interface module that receives a first input and communicates the first operational settings, and a first control module that selectively adjusts the first operational settings based on the first input and second operational settings.

Systems and methods may include a stationary supply unit including a second fluid system that is configured to fluidly couple to the fluid transfer conduit to transfer fluid with respect to the mouth via the mouthpiece based on the second operational settings, a second interface module that receives a second input and communicates the second operational settings with the portable supply unit, and a second control module that selectively adjusts the second operational settings based on the second input and the first operational settings.

This disclosure is merely illustrative in nature and is in no way intended to limit the disclosure, its application, or uses. For purposes of clarity, the same reference numbers have used in the drawings to identify comparable elements. As used herein, the arrangement and order of the embodiments herein are merely examples, and embodiments having a different arrangement or order are contemplated without altering the principles of the present disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" may encompass both an orientation of above and below. The device may be otherwise oriented (rotated 90 degrees or at other orientations) and the spatially relative descriptors used herein interpreted accordingly.

What is claimed is:

1. A system for managing fluid transfer with respect to first and second bodily regions, comprising:
    an anchoring member having a central perimeter and configured to conformingly engage the first and second bodily regions, wherein the anchoring member includes a U-shaped, unitary anchor structure; and
    a connector member including a capture portion and a fluid transfer portion, the capture portion forming a cavity around an entirety of the central perimeter of the anchoring member to provide multi-directional flow between the cavity and the entirety of the central perimeter, and the fluid transfer portion being fluidically connected to a supply source.

2. The system of claim 1, further comprising a source tubing connecting the fluid transfer portion to the supply source.

3. The system of claim 1, wherein the first bodily region includes a first outer side of a gum line of a mouth and the second bodily region including a second outer side of the gum line of the mouth, the first outer side and second outer side being on opposing sides of the gum line.

4. The system of claim 1, wherein the first bodily region includes a first cheek side of a mouth and the second bodily region includes a second cheek side of the mouth, the first and second cheek sides being on opposing sides of the mouth.

5. The system of claim 1, wherein the first bodily region includes at least one of first and second cheek areas of a mouth and the second bodily region includes at least one of first and second sides of a gum line of the mouth.

6. The system of claim 1, wherein the first bodily region includes a lower dental arch adjacent a first tooth on a first side of a mouth, and the second bodily region includes the lower dental arch adjacent a second tooth on a second side of the mouth.

7. The system of claim 1, wherein the anchoring member includes a hydrophilic material configured to be received in the cavity of the connect or member.

8. The system of claim 1, wherein the capture portion includes a distal opening configured to be positioned around the central perimeter of the anchoring member.

9. A system for managing fluid transfer with respect to first and second bodily regions, comprising:
- an anchoring member having a central perimeter and configured to conformingly engage the first and second bodily regions, wherein the anchoring member includes a U-shaped, unitary anchor structure; and
- a connector member including a capture portion and a fluid transfer portion, the capture portion forming a cavity around an entirety of the central perimeter of the anchoring member to provide multi-directional flow between the cavity and the entirety of the central perimeter.

10. The system of claim 9, further comprising a supply source including source tubing configured to connect to the fluid transfer portion.

11. The system of claim 9, further comprising a source tubing connecting the fluid transfer portion to a supply source.

12. The system of claim 9, wherein the first bodily region includes a first side of a gum line of a mouth and the second bodily region including a second side of the gum line of the mouth, the first side and second side being on opposing sides of the gum line.

13. The system of claim 9, wherein the first bodily region includes a first cheek side of a mouth and the second bodily region includes a second cheek side of the mouth, the first and second cheek sides being on opposing sides of the mouth.

14. The system of claim 9, wherein the first bodily region includes at least one of first and second cheek areas of a mouth and the second bodily region includes at least one of first and second sides of a gum line of the mouth.

15. The system of claim 9, wherein the first bodily region includes a lower dental arch adjacent a first tooth on a first side of a mouth, and the second bodily region includes the lower dental arch adjacent a second tooth on a second side of the mouth.

16. The system of claim 9, wherein the anchoring member includes a hydrophilic material configured to be received in the cavity of the connect or member.

17. The system of claim 9, wherein the capture portion includes a distal opening configured to be positioned around the central perimeter of the anchoring member.

18. A method comprising:
- providing an anchoring member including a central perimeter, and a connector member including a capture portion and a fluid transfer portion, wherein the anchoring member includes a U-shaped, unitary anchor structure;
- positioning the capture portion of the connector member so that the capture portion forms a cavity around an entirety of the central perimeter of the anchoring member;
- conformingly engaging, by the anchoring member, first and second bodily regions; and
- providing multi-directional flow between the cavity and the entirety of the central perimeter.

19. The method of claim 18, further comprising:
- providing a supply source including source tubing configured to connect to the fluid transfer portion.

20. The method of claim 18, wherein the anchoring member includes a hydrophilic material configured to be received in the cavity of the connector member.

* * * * *